(12) United States Patent
Heacock et al.

(10) Patent No.: US 11,346,786 B2
(45) Date of Patent: May 31, 2022

(54) HIGH PRESSURE SENSITIVE COLOR CHANGEABLE INDICATORS AND METHODS OF MAKING SUCH INDICATORS

(71) Applicant: Sensor International, LLC, Snoqualmie, WA (US)

(72) Inventors: Gregory L. Heacock, Maple Valley, WA (US); Andrew Mills, Holywood (GB)

(73) Assignee: SENSOR INTERNATIONAL, LLC, Snoqualmie, WA (US)

(*) Notice: Subject to any disclaimer, the term of this patent is extended or adjusted under 35 U.S.C. 154(b) by 628 days.

(21) Appl. No.: 16/155,603

(22) Filed: Oct. 9, 2018

(65) Prior Publication Data

US 2020/0110036 A1 Apr. 9, 2020

(51) Int. Cl.
*G01N 21/78* (2006.01)
*A61L 2/28* (2006.01)
*G01N 21/80* (2006.01)

(52) U.S. Cl.
CPC .............. *G01N 21/78* (2013.01); *A61L 2/28* (2013.01); *G01N 21/80* (2013.01)

(58) Field of Classification Search
CPC .......... G01N 21/78; G01N 21/80; G01N 1/30; A61L 2/28
See application file for complete search history.

(56) References Cited

U.S. PATENT DOCUMENTS

| 3,018,611 A | 1/1962 | Biritz |
| 2,768,976 A | 10/1973 | Hu |
| 3,768,976 A | 10/1973 | Hu |
| 3,899,295 A | 8/1975 | Halpern |
| 3,939,968 A | 2/1976 | Ryder |

(Continued)

FOREIGN PATENT DOCUMENTS

| CN | 101479584 | 7/2009 |
| CN | 101501468 | 8/2009 |

(Continued)

OTHER PUBLICATIONS

International Search Report in PCT Application No. PCT/US2019/054566, dated Dec. 18, 2019.

(Continued)

*Primary Examiner* — Dennis White
(74) *Attorney, Agent, or Firm* — McAndrews, Held & Malloy, Ltd.

(57) ABSTRACT

The present technology includes a color changeable indicator that changes color upon exposure of the indicator to high pressure and comprises at least one reagent releasing layer, a transition layer disposed on the reagent releasing layer, a color changeable layer disposed on the transition layer, and a non-porous protectant encompassing the reagent releasing layer, the transition layer and the color changeable layer. An additional reagent releasing layer can be located between the transition layer and the color changeable layer. The indicators provide simple, reliable, and cost effective detection means for detecting whether a product has been exposed to high pressure, e.g. high pressure pasteurization, and may find use in applications such as food and beverage processing and/or packaging and medical applications.

29 Claims, 12 Drawing Sheets

(7 of 12 Drawing Sheet(s) Filed in Color)

(56) References Cited

U.S. PATENT DOCUMENTS

| | | |
|---|---|---|
| 4,003,709 A | 1/1977 | Eaton |
| 4,098,577 A | 7/1978 | Halpern |
| 4,135,792 A | 1/1979 | Deeg et al. |
| 4,526,752 A | 7/1985 | Perlman et al. |
| 4,692,309 A | 9/1987 | Pannwitz |
| 4,728,499 A | 3/1988 | Fehder |
| 5,159,360 A | 10/1992 | Stoy et al. |
| 5,518,927 A | 5/1996 | Malchesky et al. |
| 5,623,323 A | 4/1997 | Johnson et al. |
| 5,706,073 A | 1/1998 | Volk |
| 5,942,438 A | 8/1999 | Antonoplos et al. |
| 6,060,210 A | 5/2000 | Eda et al. |
| 6,114,509 A | 9/2000 | Olsen et al. |
| 6,132,086 A | 10/2000 | Henwood |
| 6,183,640 B1* | 2/2001 | Wang .............. B01D 67/0011 210/500.27 |
| 6,218,189 B1 | 4/2001 | Antonoplos et al. |
| 6,232,128 B1* | 5/2001 | Iguchi .............. B65D 79/02 436/163 |
| 6,254,969 B1 | 7/2001 | Eberle |
| 6,270,724 B1 | 8/2001 | Woodaman |
| 6,518,231 B2 | 2/2003 | Appel et al. |
| 6,634,747 B1 | 10/2003 | Atkins et al. |
| 6,634,753 B1 | 10/2003 | Rozenman |
| 6,710,221 B1 | 3/2004 | Pierce et al. |
| 6,790,411 B1 | 9/2004 | Forest et al. |
| 6,851,808 B2 | 2/2005 | Heacock |
| 7,166,565 B2 | 1/2007 | Caswell et al. |
| 7,188,685 B2* | 3/2007 | Downton ........... E21B 7/067 175/104 |
| 7,219,799 B2 | 5/2007 | Bonnette et al. |
| 7,244,252 B2 | 7/2007 | Berndt |
| 7,785,299 B2 | 8/2010 | Crawford et al. |
| 8,137,303 B2 | 3/2012 | Crawford et al. |
| 8,163,237 B2 | 4/2012 | Crawford et al. |
| 8,257,663 B2 | 9/2012 | Crawford et al. |
| 8,338,131 B2 | 12/2012 | Callen |
| 8,388,131 B2 | 3/2013 | Heacock |
| 8,663,998 B2 | 3/2014 | Heacock |
| 9,746,421 B2 | 8/2017 | Heacock |
| 2002/0022008 A1 | 2/2002 | Forest et al. |
| 2002/0023642 A1 | 2/2002 | Holmsten et al. |
| 2002/0137123 A1 | 9/2002 | Hui |
| 2003/0199095 A1 | 10/2003 | Yuyama |
| 2004/0115319 A1 | 6/2004 | Morris |
| 2004/0180391 A1 | 9/2004 | Gratzl et al. |
| 2005/0041200 A1 | 2/2005 | Rich |
| 2005/0125924 A1 | 6/2005 | Benjamin et al. |
| 2005/0164898 A1 | 7/2005 | Kalsuri et al. |
| 2006/0046301 A1 | 3/2006 | Happe |
| 2006/0054525 A1 | 3/2006 | Dean et al. |
| 2006/0054526 A1 | 3/2006 | Dean |
| 2006/0069305 A1 | 3/2006 | Couvillon, Jr. et al. |
| 2006/0110835 A1 | 5/2006 | Gohil |
| 2006/0181676 A1 | 8/2006 | Tucker et al. |
| 2006/0236913 A1 | 10/2006 | Willis |
| 2007/0017042 A1 | 1/2007 | Cincotta et al. |
| 2007/0140911 A1 | 6/2007 | Carney et al. |
| 2008/0081020 A1 | 4/2008 | Huang |
| 2008/0129960 A1 | 6/2008 | Heacock |
| 2009/0266289 A1 | 10/2009 | Greene |
| 2009/0301382 A1 | 12/2009 | Patel |
| 2009/0303440 A1 | 12/2009 | Heacock et al. |
| 2010/0112680 A1 | 5/2010 | Brockwell et al. |
| 2011/0130727 A1 | 6/2011 | Crawford et al. |
| 2011/0130728 A1 | 6/2011 | McKinnon et al. |
| 2011/0259086 A1 | 10/2011 | Harris et al. |
| 2012/0276647 A1 | 1/2012 | Mills |
| 2013/0130399 A1 | 5/2013 | Mills |
| 2013/0150785 A1 | 6/2013 | Heacock |
| 2013/0269592 A1 | 10/2013 | Heacock et al. |
| 2013/0293353 A1 | 11/2013 | McPherson |
| 2014/0158039 A1* | 6/2014 | Kasper .............. G09F 3/0291 116/206 |
| 2014/0243262 A1* | 8/2014 | Bindra .............. A61K 9/20 514/6.5 |
| 2014/0296402 A1 | 10/2014 | Jung |
| 2014/0311400 A1* | 10/2014 | Park .............. G01K 3/04 116/216 |
| 2015/0087076 A1 | 3/2015 | Heacock |
| 2015/0225304 A1 | 8/2015 | Donze |
| 2015/0253252 A1 | 9/2015 | Smyth |
| 2015/0346513 A1 | 12/2015 | Heacock |
| 2016/0011157 A1 | 1/2016 | Smyth |
| 2016/0327491 A1 | 11/2016 | Wood |

FOREIGN PATENT DOCUMENTS

| | | |
|---|---|---|
| EP | 0231499 | 8/1987 |
| EP | 2021755 | 5/2007 |
| WO | 02099416 A1 | 12/2002 |
| WO | 2004077035 | 9/2004 |
| WO | 2007018301 | 2/2007 |
| WO | 2008095960 | 8/2008 |
| WO | 2008067143 | 10/2008 |
| WO | 2013085655 | 6/2013 |
| WO | WO-2013106234 A2* | 7/2013 .......... G06F 3/03545 |
| WO | 2015048138 | 4/2015 |
| WO | WO2018106234 A1 | 6/2018 |

OTHER PUBLICATIONS

Michael Freemantle, Intelligence Ink Detects Oxygen, Chemical Gas Sensing, Aug. 2, 2004, p. 11, vol. 82, No. 31, Chemical & Engineering News USA (2 pages).

Swann et al., "Designing Out Curative Syringe Reuse: Maximising Global Acceptance and Impact by Design," Internet Citation, http://eprints.hud.ac.uk/11783/ [dated Sep. 18, 2013] abstract.

The Guardian, Architecture and Design Blog with Oliver Wainwright, "How colour-changing technology could revolutionise the medical industry," Internet Citation, http://www.theguardian.cco/artanddesign/architectarc-design-blog/2013/aug/28/colour-changing-syringe-medical-design [dated Sep. 18, 2013].

International Preliminary Report on Patentability for PCT/US2019/054655, dated Apr. 22, 2021, 10 pages.

* cited by examiner

HIGH PRESSURE SENSITIVE COLOR CHANGEABLE INDICATORS AND METHODS OF MAKING SUCH INDICATORS

CROSS-REFERENCE TO RELATED APPLICATIONS

[Not Applicable]

FEDERALLY SPONSORED RESEARCH OR DEVELOPMENT

[Not Applicable]

BACKGROUND OF THE APPLICATION

Pasteurization is a partial sterilization process to make a product (e.g. a food, beverage, pharmaceutical or medical device) safe for use or consumption and/or to improve its shelf-life. It is a process in which packaged or non-packaged products (e.g. foods, beverages, pharmaceuticals or medical devices) are treated to eliminate pathogens. It is intended to reduce spoilage organisms and eliminate vegetative bacteria. It is used widely in the dairy industry and other food processing industries to achieve food preservation and food safety.

There are different types of pasteurization. For example, a common type of pasteurization is thermal pasteurization that uses heat to accomplish partial sterilization. For example, many liquid products are heat treated in a continuous system where heat can be applied using a plate heat exchanger and/or direct or indirect use of steam and hot water. However, the heat used during pasteurization causes minor changes to the nutritional quality of foods as well as the sensory characteristics. As such, other methods of pasteurization are also sometimes desired. One example is High Pressure Processing (HPP), which uses high pressure to accomplish pasteurization usually using high hydrostatic pressure in which the pasteurization is accomplished using application of pressure or force exerted by fluid over time Within a living microorganism, e.g. a bacteria cell, many pressure sensitive processes such as protein function, enzyme action, and cellular membrane function take place. These functions are impacted by high pressure resulting in the inability of the bacteria to survive. During HPP, products, e.g. foods and beverages, are subjected to pressures from about 200 MPa to above 600 MPa (29,000 psi to 87,000 psi) for a specified time. This pressure destroys pathogenic microorganisms by interrupting their cellular functions. However, small macromolecules that are responsible for flavor, odor, and nutrition are typically not changed by pressure.

HPP is popular within the food industry because of its ability to inactivate pathogenic microorganisms with minimal to no heat treatment, resulting in the almost complete retention of nutritional and sensory characteristics of food without sacrificing shelf-life. Other advantages of HPP are that pressure transmission is instantaneous and uniform, it is not controlled by product size and is effective throughout the entirety of the food item. Thus, HPP offers several advantages over traditional thermal processing including: reduced process times; minimal heat damage effects; retention of freshness, flavor, texture, and color; and minimal vitamin loss. Further, the HPP processing allows the food processor to use labeling that is "clean", i.e., additive and or preservative free, which is a big driver of the technology.

Color changeable indicators are used to detect certain trigger substances (e.g. the presence of acid or gases such as carbon dioxide or ammonia) in an environment and are particularly important in, amongst other things, medical applications and food and drug packaging. These color changeable indicators typically rely on reactive dyes or pigments. These dyes or pigments can exist in at least two different chemical states each having a different color. When the dye or pigment is in the first chemical state it appears a first or initial color. When the dye or pigment is exposed to the substance that it is intended to detect, it undergoes a chemical reaction to form the second chemical state. In the second chemical state the dye or pigment appears a second or triggered color. In this manner it indicates the presence of the substance that it is intended to detect.

Various color changeable indicators and related apparatuses have been described in applications and patents co-owned by applicant. These patents, applications and their related cases are incorporated herein by reference. U.S. Pat. No. 8,388,131 describes, for example, a disposable limited or restricted use apparatus that includes a color changeable portion wherein the time that the color change occurs is controlled so that it coincides to the approximate time of the end of one use of a single use apparatus or to the approximate expiration time for extended but limited or restricted use apparatus. U.S. patent application Ser. No. 14/292,246, for example, describes carbon dioxide sensing color change indicators for use with disposable, limited use, or restricted use apparatuses. U.S. Pat. No. 9,746,421 describes, for example, use protocol indicators having a color changeable dye that changes color after exposure to a particular environment for a defined or predetermined time and an exposure time indicator that uses a color changeable dye or multiple color changeable dyes that change color after exposure to an environment in a sequential manner. U.S. patent application Ser. No. 15/832,379, for example, deals with color changeable indicator particles having a particulate organic core with at least one color changeable indicator coated on the organic core and polymeric composites made using such color changeable indicator particles. U.S. patent application Ser. No. 15/934,527, for example, deals with color changeable materials incorporated into adhesive materials. U.S. patent application Ser. No. 15/295,431, for example, deals with a color changing sensor that delays color change via a self-contained gas layer or gas-containing substrate that interferes with the exposure of the color change indicator to atmospheric conditions and/or allows for activation of the color change sensor by the user.

During and after product processing it is desirable, to have an indication of whether that product has undergone pasteurization, e.g. HPP. In some instances, it is also a regulatory requirement to know that a product has met the validated process HPP parameters. Indicators can be included on a product or packaging that change color following exposure to high pressure, e.g. during or after HPP. This clearly indicates to the user or processor that the product has been exposed to a specific high pressure, e.g. undergone HPP. Do to the minimal impact of HPP to the products sensory qualities it is often difficult to visually tell processed from unprocessed product.

Specifically, during and after processing of packaged or non-packaged products (e.g. foods, beverages, pharmaceuticals or medical devices), it is often advantageous and is often a regulatory requirement to know whether the product has gone through HPP. It can also be helpful to know whether the product has been exposed to a sufficient level of pressure during HPP, and in many instances it is a mandatory regulatory requirement to know. This allows one to understand, document, and verify, e.g. per regulatory requirements, whether the product has been treated or sufficiently treated to reduce or eliminate pathogens, spoilage organisms, vegetative bacteria, etc. As such, a simple, reliable, and cost effective mechanism is desired for detecting and indicating whether a product has been exposed to or subjected to high pressure, e.g. HPP, and/or whether such exposure or treatment has been adequate.

SUMMARY

The present application deals with pressure sensitive color changeable indicators that change from a first initial color to a second color in response to exposure to high pressure, e.g. during or after HPP, including for a particular period of time. These indicators make use of a color changeable layer, e.g. a color changeable composite/film made from color changeable pigments, dyes, or color changeable particles. The color changeable layer, e.g. color changeable film, is used with at least one reagent releasing layer that releases a reagent that upon exposure to high pressure, e.g. an acid releasing tablet that releases a reagent or reagents upon exposure to high pressure. The color changeable layer, e.g. color changeable film, is configured to change color upon exposure to the reagent that is released from the reagent releasing layer, e.g. acid, or a reaction product between reagents released from multiple reagent releasing layers, e.g. carbon dioxide released from reaction of acid and base from two reagent releasing layers. In one embodiment, a transition layer separates the color changeable layer, e.g. color changeable film, and the reagent releasing layer, e.g. acid releasing tablet, to avoid premature color change. In another embodiment, a transition layer separates multiple reagent releasing layers, e.g. an acid releasing tablet and a base releasing tablet, preventing their reaction to avoid premature color change. In certain embodiments, a protectant encompasses or surrounds the color changeable material, the transition layer and reagent releasing layer to prevent environmental interference with the materials within the indicator. The protectant may also prevent the color changeable layer from reverting back to its original color after it has been triggered by high pressure. The indicators provide simple, reliable, and cost effective detection means for detecting whether a product has been exposed to high pressure, e.g. HPP, and may find use in applications such as food and beverage processing and/or packaging and medical applications.

An embodiment of the present color changeable indicator comprises a reagent releasing layer, a transition layer disposed on said reagent releasing layer, and a color changeable layer disposed on said transition layer, wherein the indicator is configured to change color upon exposure of the indicator to high pressure, e.g. at least 450 MPa, at least 525 MPa, at least 600 MPa, etc. The color changeable indicator can be configured to change color upon exposure of the indicator to high pressure pasteurization. The color changeable layer can be a color changeable film, e.g. a pH indicator.

In one embodiment, the reagent releasing layer comprises an acid and water releasing tablet releasing tablet and the transition layer comprises a permeable membrane. The acid and water releasing tablet can comprise an organic acid, hydrated particles, and polymer binder particles. The hydrated particles can be silica gel particles that are hydrated to between 70% and 71% by weight. For example, the organic acid can be camphor sulfonic acid (CPA), benzene sulfonic acid, sulfanilic acid and/or toluene sulfonic acid (TSA). For example, the polymer binder particles can be polycaprolactone, polytetrafluoro ethylene, polyvinyl alcohol, hydroxyl ethyl cellulose, polyethylene oxide, polyethylene, low density polyethylene, polylactide, poly vinyl pyridine and/or cellulose nitrate. The transition layer can be a permeable membrane that has a pore size of up to about 0.2 microns or up to about 0.03 microns In another embodiment, the reagent releasing layer comprises an acid releasing tablet and the transition layer is a permeable hydrated layer. For example, the organic acid can be camphor sulfonic acid (CPA), benzene sulfonic acid, sulfanilic acid and/or toluene sulfonic acid (TSA). The permeable hydrated layer permeable hydrated layer can be a silica doped hydrated layer. The silica doped hydrated layer can comprise silica gel particles and binder particles. The silica gel particles can be hydrated to between 70% and 71% by weight. For example, the binder particles can be paper and/or polymer binder particles Another embodiment of the color changeable indicator comprises a first reagent releasing layer, one or more additional reagent releasing layers, a transition layer disposed between said reagent releasing layers, a color changeable layer disposed on one of said reagent releasing layers, wherein the indicator is configured to change color upon exposure of the indicator to high pressure, e.g. at least 450 MPa, at least 525 MPa, at least 600 MPa, etc. The color changeable indicator can be configured to change color upon exposure of the indicator to high pressure pasteurization. The color changeable layer can be a color changeable film, e.g. a pH indicator.

In one embodiment, the reagent releasing layer comprises an acid releasing tablet, the additional reagent releasing layer comprises a sodium bicarbonate tablet and the transition layer is a non-permeable material in the form of a washer or a perforated disc. For example, the organic acid can be camphor sulfonic acid (CPA), benzene sulfonic acid, sulfanilic acid and/or toluene sulfonic acid (TSA).

Embodiments discussed herein, e.g. above, can further comprise a protectant encompassing the reagent releasing layer, transition layer and color changeable layer. The protectant can be vacuum sealed around the other layers. In some embodiments, an adhesive can also be applied to the protectant or bottom layer to apply the indicator to a substrate.

The color changeable indicators disclosed herein, e.g. above, can be incorporated into or onto a packaging or product.

These and other advantages and novel features of the present invention, as well as details of illustrated embodiments thereof will be more fully understood from the following description and from the figures.

BRIEF DESCRIPTION OF SEVERAL VIEWS OF THE DRAWINGS

The patent or application file contains at least one drawing executed in color. It is understood that copies of this patent or patent application publication with color drawing(s) will be provided by the Office upon request and payment of the necessary fee.

Figure 1A:
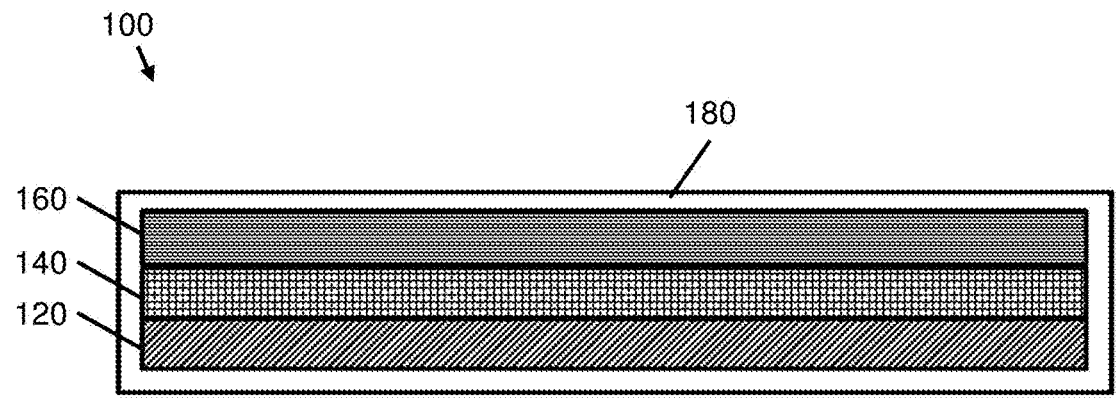
FIGS. 1A and 1B show embodiments of the present color changeable HPP indicators.

The foregoing summary, as well as the following detailed description of certain embodiments of the present application, will be better understood when read in conjunction with the appended drawings. For the purposes of illustration, certain embodiments are shown in the drawings and described herein. It should be understood, however, that the claims are not limited to the arrangements and instrumentality shown in the attached drawings or the detailed description. Furthermore, the appearance shown in the drawings is one of many ornamental appearances that can be employed to achieve the stated functions of the system.

DETAILED DESCRIPTION

The present technology relates to pressure sensitive color changeable indicators or sensors that change from a first initial color to a second color in response to exposure to high pressure, e.g. during or after HPP. For example, the pressure sensitive color changeable indicators or sensors change color in response to exposure to high pressures from about 200 MPa to above 600 MPa. Other high pressures including high hydrostatic pressures utilized during high pressure pasteurization are also included. These indicators make use of a color changeable layer combined with at least one reagent releasing layer, which comprises and is configured to release a reagent (or reagents) upon exposure to the high pressures associated with HPP. The color changeable layer changes color upon exposure to the reagent that is released from the reagent releasing layer or upon exposure to a reaction product of reagents released from multiple reagent releasing layers. A transition layer separates the color changeable layer and the reagent releasing layer or separates multiple reagent releasing layers to avoid premature color change. A protectant encompasses the color changeable material, transition layer and reagent releasing layer. This layer may prevent drying out and/or environmental interference with the indicator.

In one embodiment, the present technology includes a color changeable indicator that changes color upon exposure of the indicator to high pressure, wherein the indicator is comprised of (1) a reagent releasing layer, (2) a transition layer disposed on the reagent releasing layer, and (3) a color changeable layer disposed on the transition layer. In some embodiments, a protectant encompassing the reagent releasing layer, the transition layer and the color changeable layer is also added. FIG. 1A shows such an embodiment of the present color changeable indicator 100 comprising a reagent releasing layer 120, a transition layer 140 disposed on the reagent releasing layer 120, a color changeable layer 160 disposed on the transition layer 140 and a protectant 180 encompassing the reagent releasing layer 120, the transition layer 140 and the color changeable layer 160.

Figure 1B:
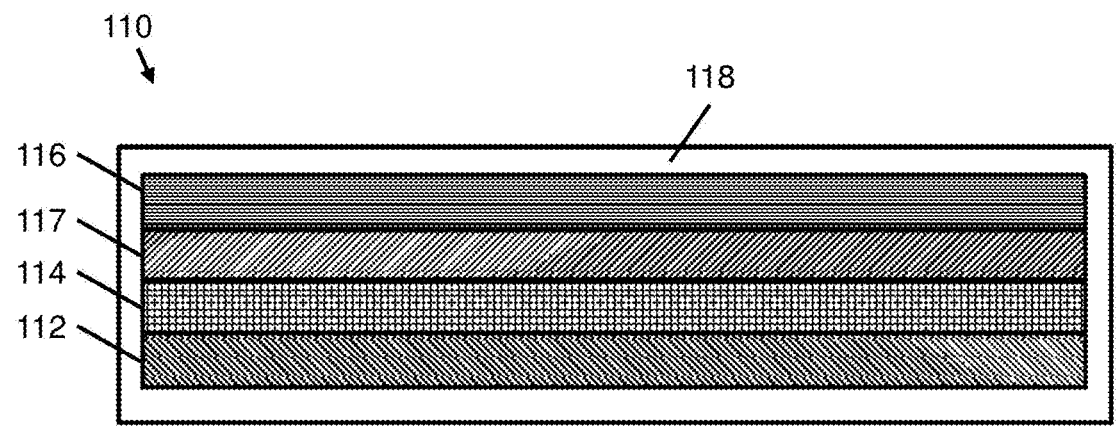

In other embodiments an additional reagent releasing layer is inserted between the transition layer and the color changeable layer. In that embodiment, the present technology includes a color changeable indicator that changes color upon exposure of the indicator to high pressure that comprises (1) a first reagent releasing layer, (2) a transition layer disposed on the reagent releasing layer, (3) a second reagent releasing layer disposed on the transition layer, and (4) a color changeable layer disposed on the second reagent releasing layer. In some embodiments, a protectant encompassing the reagent releasing layers, the transition layer and the color changeable layer is also added. FIG. 1B shows such an embodiment of the present color changeable indicator 110 comprising a first reagent releasing layer 112, a transition layer 114 disposed on the reagent releasing layer 112, a second reagent releasing layer 117 disposed on the transition layer 114, a color changeable layer 116 disposed on the second reagent releasing layer 117 and a protectant 118 encompassing the reagent releasing layers 112 and 117, the transition layer 114 and the color changeable layer 116.

Reagent Releasing Layers

The reagent releasing layer or layers is a layer that comprises a reagent or reagents and is configured to release a reagent or reagents upon exposure to high pressure, e.g. when the indicator undergoes HPP. In one embodiment, the released reagent then reacts with a color changeable material (e.g. color changeable pigments, dyes, or particles) on or in the color changeable layer in order to cause a color change in the color changeable layer and indicate that the indicator has been exposed to high pressure. In another embodiment, the released reagent then reacts with one or more other released reagents, to form a reaction product that reacts with a color changeable material (e.g. color changeable pigments, dyes, or particles) on or in the color changeable layer in order to cause a color change in the color changeable layer and indicate that the indicator has been exposed to high pressure.

The released reagent can be any substance that reacts with a color changeable material to cause a color change or reacts to form a reaction product that reacts with a color changeable material to cause a color change. Examples of possible reagents include acids, bases, water, carbon dioxide, oxygen, ammonia, oxygen, and color-forming agents, such as complexing agents. In some embodiments, the released reagent is an acidic or basic reagent that causes a change in pH within the indicator environment. In these embodiments, the color changeable material is a pH status indicator that changes color based on changes in pH within the indicator environment.

In some embodiments, the reagent releasing layer is in the form of a solid tablet. The tablet can be formed by compressing the components using a die or press. Examples of reagent releasing tablets include an acid and water releasing tablet, an acid releasing tablet, a base releasing tablet, a base and water releasing tablet, a water releasing tablet, and/or a gas (e.g., carbon dioxide or ammonia) releasing tablet.

In one embodiment, an acid and water releasing tablet of the present technology comprises an organic acid, hydrated silica gel particles, and polymer binder particles. The three components are combined and compressed in a die or press to form a solid tablet. Other nonreactive components may also be included. In another embodiment, an acid releasing tablet comprises an acid that is compressed with a polymer binder in a die or press to form a solid tablet. In yet another embodiment, a base releasing tablet comprises base that is compressed with a polymer binder in a die or press to form a solid tablet.

The acid can be any acid suitable for forming an acid or acid and water releasing tablet. For example, it can be camphor sulfonic acid (CPA), benzene sulfonic acid, sulfanilic acid, toluene sulfonic acid (TSA), and/or perfluorooctanoic acid.

The base can be any base suitable for forming a base or base and water releasing tablet. For example, it can be any hydroxide, bicarbonate or carbonate, e.g., sodium hydroxide, sodium bicarbonate and/or sodium carbonate. The base can also be hydroxide, bicarbonate, carbonate salts of quaternary cations e.g., benzyltrimethyl ammonium, trioctylmethyl ammonium, tricaprylmethyl ammonium, tetraoctyl ammonium, tetrabutyl ammonium, cetyltrimethyl ammonium, tetrahexyl ammonium, tetraphenyl phosphonium, trioctyl phosphonium and/or hexadecyl tributyl phosphonium.

The hydrated particles can be any powder material that can function as a desiccant, for example, silica gel, activated carbon, activated alumina, calcium sulfate, calcium chloride, molecular sieves, and/or super absorbent polymers, such as sodium polyacrylate. The hydrated particles are typically hydrated using distilled and/or deionized water. The hydrated particles, e.g. silica gel particles, are preferably hydrated to about 60-80% by weight, preferably about 65-75%, more preferably about 68%-72%, most preferably about 70-71%. The hydrated particles, e.g. silica gel particles, can have a particle size of about 0.1 to about 1000 microns, preferably about 1 to about 100 microns, preferably about 1 to about 10 microns, preferably about 25 microns.

The polymer binder can be, for example, polycaprolactone, polytetrafluoro ethylene, polyvinyl alcohol, hydroxyl ethyl cellulose, polyethylene oxide, polyethylene, low density polyethylene, polylactide, poly vinyl pyridine and/or cellulose nitrate. The polymer binder particles can have a particle size of about 0.1 to about 1000 microns, preferably about 1 to about 100 microns, preferably about 1 to about 10 microns, preferably about 25 microns.

Color Changeable Layer

The present color changeable layer incorporates a color changeable material. In one embodiment, the color changeable layer may comprise a substrate with a color changeable material disposed on that substrate. In another embodiment, the color changeable layer has the color changeable material incorporated into it, e.g. a color changeable polymeric composite or film with the color changeable material incorporated into it (as disclosed in U.S. patent application Ser. No. 15/832,379 which is incorporated herein in its entirety).

Color changeable materials include pigments, dyes or color changeable particles coated with such pigments or dyes. Various pigments or dyes can be used as or in the present color changeable material. The color changeable material can respond to changes in pH and/or the presence of different reagents, such as carbon dioxide, oxygen, complexing agents and ammonia.

As discussed above, in some embodiments, the color changeable material is a pH status indicator. A pH status indicator is a compound that changes color when exposed to a change in pH and is used to indicate a change in environment. A pH status indicator is a halochromic chemical compound that is added in small amounts to a solution so that the pH of the solution can be determined visually. A pH status indicator is a chemical detector for hydronium ions ($H_3O^+$) or hydrogen ions ($H^+$) in the Arrhenius model. Normally, the indicator causes the color of the solution to change depending on the pH. The reactions of pH indicators can be simplified as follows:

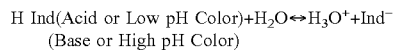

These reactions and their role in the present color changeable dye will be discussed in more detail below.

As an example of how the pH status indicators function in different environments, for Cresol Red the acid or low pH color is yellow and the base or high pH color is reddish purple. When the Cresol Red is in an acidic environment, it will be in the H Ind form which is the acid or low pH color of yellow. When placed in a basic environment, the Cresol Red changes to its Ind– form which is the base or high pH color of reddish purple. This would apply similarly to the other pH status indicators.

Examples of pH sensitive, carbon dioxide (acid) reactive pigments and dyes include, but are not limited to, m-Cresol Purple (MCP, Hydroxy triarylmethane), Thymolphthalein (3,3-bis(4-hydroxy-2-methyl-5-propan-2-ylphenyl)-2-benzofuran-1-one), o-Cresolphthalein, Acryloly florescein (AcFl), β-methyl umbelliferon (BMUB), Bromothymol blue (BTB, Hydroxy triarylmethane), 5' and 6'-Carboxyseminaphtholfluorescein (c-SNAFL), 5' and 6'-Carboxyseminaphtholrhodamine (c-SNARF), Cresol Red (CR, o-Cresolsulfonephthalein), Hexadecyl trimethyl ammonium cation ($CTA^+$), Hexadecyl trimethyl ammonium hydroxide (CTAH), Dual lumophore referencing (DLR), 2-(2,4-Dinitrophenylaxo)-1-naphthol-3,6disulphonic acid (DNPA), tris (thenoyltrifluoroacetonato) europium (III) ($[Eu(tta)_3]$), Fluorescein (Fl, resorcinolphthalein), 7-hydroxycoumarin-4-acetic acid (HCA), 1, Hydroxypyrene-3,6,8-trisulphonic acid (HPTS), Neutral red (NR, toluylene red), Phenol Red (PR, phenolsulfonphthalein), Rhodamine 6G (R6G), Sulforhodamine 101 (SRh), Thymol blue (TB, thymolsulphonephthalein), and/or Texas Red hydrazine (THR).

Examples of fluorimetric pH sensitive, carbon dioxide reactive pigments and dyes include but are not limited, to 1-hydroxypyrene-3,6,8-trisulphonate, 1,3-dihydroxypyrene-6,8-disulphonate, fluorescein, umbelliferone, 4-methylumbelliferone, 3-benzothiazoylbelliferone, 7-hydroxycoumarin-3-carboxylic acid, 1-naphthol-2-sulphonate, 1-naphthol-4-sulphonate, 2-naphthol-6-sulphonate, 7-hydroxyflavone, 7-hydroxyisoflavone, 3-hydroxyxanthone, 3,6-dihydroxyxanthone, 7-hydroxy-4-methylchromon, 7-hydroxylepidone, 3-hydroxyxacridone, harmol methoiodide, salicylaldehyde semicarbazone and 2-hydroxycinnamic acid.

Examples of pH sensitive, ammonia/amine (base) reactive pigments and dyes include, but are not limited to, Phloxine B, Methyl yellow, Bromophenol blue, Congo red, Methyl Orange, Bromochlorophenol blue, Ethyl orange, Fluorescein, Bromocresol green, Chrysoidin, Methyl red, Alizarin red, Cochineal, Chlorophenol red, Bromocresol purple, 4-Nitrophenol, Alizarin, Nitrazine yellow, Bromothymol blue, Brilliant yellow, Neutral red, Rosolic acid, Phenol red, m-Cresol purple, Thymol blue, Xylenol blue and Cresol red.

Various color change indicators have been described in applications and patents co-owned by applicant. These patents, applications and their related cases, including the color changeable materials described therein, are incorporated herein by reference: U.S. Pat. Nos. 8,388,131, 8,663,998, 9,746,421 and U.S. patent application Ser. Nos. 14/292,246, 15/295,431, 15/832,379, 15/934,527.

The color changeable material, e.g. pigment, dye and/or particle, may be present with other components. For example, acids or bases can be combined with the color changeable material. Examples of acids that can be added to the present color changeable material include inorganic acids such as: hydrocholoric, nitric, sulfuric, perchloric, phosphoric acids and organic acids, such as: formic, acetic, tartaric, ascorbic, propanoic, butyric, valeric, oxalic, amlic, citric, benzoic, camphor sulfonic acid (CPA), benzene sulfonic acid, sulfanilic acid, toluene sulfonic acid (TSA), perfluorooctanoic acid, succinic, uric, salicylic, and triflic acids. Examples of bases that can be added to the present color changeable material include hydroxide, bicarbonate, carbonate salts of quaternary cations such as benzyltrimethyl ammonium, trioctylmethyl ammonium, tricaprylmethyl ammonium, tetraoctyl ammonium, tetrabutyl ammonium, cetyltrimethyl ammonium, tetrahexyl ammonium, tetraphenyl phosphonium, trioctyl phosphonium and hexadecyl tributyl phosphonium. In making the $CO_2$-sensing adhesive, the hydroxide salt of these cations are generally preferred, for example, tetraoctyl ammonium hydroxide, TOAOH, or tetra butyl ammonium hydroxide, TBAOH. Other components could also be added to the color changeable material composition, e.g. solvents, polymers, etc.

In one embodiment, the color changeable material is a color changeable particle that comprises a core and at least one color changeable pigment or dye coated on the core. For example, in one embodiment, the core can be an organic polymer particle (discussed herein, for example, as an organic core polymer or organic polymer core) having a melting point below about 200° C. In another embodiment, the core can be an inorganic core. In another embodiment, the color changeable material can have a mixture or organic and inorganic cores.

The particulate organic core polymer can be, for example, low density polyethylene (LDPE), linear low density polyethylene (LLDPE), high density polyethylene (HDPE), isotactic polymethyl methacrylate (IPMMA), polymethyl methacrylate (PMMA), polystyrene (PS), polypropylene (PP), polyvinylidene fluoride (PVDF), polyoxymethylene (POMH), polybutene-1 (PB), nylon 11 (PA 11), nylon 12 (PA 12), ethylene-vinyl acetate (EVA), polycaprolactone (PCL), polyethylene oxide (PEOX), polypropylene oxide (PPDX) or mixtures thereof. Exemplary polymers and their melting points are listed in Table 1. As discussed further below, it is understood that the melting temperatures of a given organic polymer may vary depending on the composition of the specific polymer used or selected. For example, polyethylene may have a melting point in the range of about 105° C. to 180° C. with low density polyethylene in the range, for example, of about 105 to 120° C. and high density polyethylene, for example, in the range of about 120 to 180° C. Likewise, polypropylene may have a melting point, for example, in the range of about 160 to 170° C.

TABLE 1

Potential Particulate Organic Core Polymers and Bulk Polymers And Melting Temperatures

| Polymer | Abbreviation | Melting temp ° C. |
|---|---|---|
| Polystyrene | PS | 240 |
| Low density polyethylene | LDPE | 120 |
| Linear low density polyethylene | LLDPE | 127 |
| High density polyethylene | HDPE | 130 |
| Isotactic polymethyl methacrylate | IPMMA | 160 |
| Polymethyl methacrylate | PMMA | 160 |
| Polypropylene | PP | 165 |
| Polyvinylidene fluoride | PVDF | 177 |
| Polyoxymethylene | POMH | 175 |
| Polybutene-1 | PB | 126 |
| Nylon 11 | PA 11 | 185 |

TABLE 1-continued

Potential Particulate Organic Core Polymers and Bulk Polymers And Melting Temperatures

| Polymer | Abbreviation | Melting temp ° C. |
|---|---|---|
| Nylon 12 | PA 12 | 175 |
| Ethylene-vinyl acetate | EVA | 72-98 |
| Polycaprolactone | PCL | 60 |
| Polyethylene oxide | PEOX | 66 |
| Polypropylene oxide | PPOX | 75 |

The particulate organic polymer used as the core polymer comprises a particle and may be available in the form of a powder comprised of particles. It is understood to a person of ordinary skill in the art that a particle has characteristics such as, for example, reduced size and typically spherical shape. The particle size of the organic core polymer particles of embodiments of the present invention can be relatively large, for example, having an average particle size of greater than about 1 micron, and preferably having an average particle size between about 10 and 1000 microns. It is known to a person of ordinary skill in the art how to prepare polymer powders with particles of appropriate size, for example, through known grinding or milling techniques. For example, the organic core polymer particles may generally have a particle size of greater than (>) about 10 microns in diameter, alternatively greater than (>) about 20 microns, alternatively greater than (>) about 50 microns, alternatively greater than (>) about 80 microns, alternatively greater than (>) about 110 microns, alternatively greater than (>) about 140 microns, alternatively greater than (>) about 170 microns, alternatively greater than (>) about 200 microns, alternatively greater than (>) about 230 microns, alternatively greater than (>) about 260 microns, alternatively greater than (>) about 290 microns, alternatively greater than (>) about 320 microns, alternatively greater than (>) about 350 microns, alternatively greater than (>) about 380 microns, alternatively greater than (>) about 410 microns, alternatively greater than (>) about 440 microns, alternatively greater than (>) about 470 microns and alternatively greater than (>) about 500 microns. In one preferred embodiment, the core polymer is LDPE with a particle size of about 250 microns. In such examples they are particulate, but not nanoparticulate and they do not need to be finely divided.

The particulate organic polymer used as the core polymer is meltable at generally low temperatures and has a melting point such that the core polymer is capable of being melted and/or extruded, for example, using known melting or extrusion techniques. The particulate organic polymer is preferably a solid at room temperature (approximately 20-22° C.) and, as discussed above, may take the form of a powder. In some embodiments, the particulate organic core polymer can have a melting point above room temperature and below about 200° C., alternatively above room temperature and below about 150° C., alternatively above room temperature and below about 100° C., alternatively above room temperature and below about 85° C. As discussed above, the melting temperatures of a given organic polymer used as the core polymer may vary depending on the composition of the specific polymer used or selected. For example, the core polymer may have a melting point in the range of about 105-180° C., about 105-120° C., about 120-180° C., or about 160-170° C. In certain embodiments, the melting point is between about 25° C. and about 200° C., alternatively about 60 to 120° C. or about 120 to 185° C., alternatively about 60-75° C.

The particulate inorganic substrate can be, for example, silicon dioxide, titanium dioxide, aluminum oxide, magnesium oxide or calcium oxide.

As discussed above, the particulate inorganic substrate used as the core comprises a particle and may be available in the form of a powder comprised of particles. It is understood to a person of ordinary skill in the art that a particle has characteristics such as, for example, reduced size and typically spherical shape. The particle size of the inorganic substrate particles of embodiments of the present invention can be 10 nm to 10 microns.

The color changeable indicator particles discussed above can be used to make a color changeable polymeric composite, such as a film, tube, sheet, ring, etc. A color changeable polymeric composite can includes at least one organic polymer; at least one color changeable indicator substantially homogeneously dispersed within the polymer wherein the polymeric composite has a melting point between about 60° C. and about 200° C., alternatively between about 85° C. and about 185° C., alternatively between about 60° C. and about 70° C., alternatively between about 70° C. and about 80° C., alternatively between about 80° C. and about 90° C., alternatively between about 90° C. and about 100° C., alternatively between about 100° C. and about 110° C., alternatively between about 110° C. and about 120° C., alternatively between about 120° C. and about 130° C., alternatively between about 130° C. and about 140° C., alternatively between about 140° C. and about 150° C., alternatively between about 150° C. and about 160° C., alternatively between about 160° C. and about 170° C., alternatively between about 170° C. and about 180° C., alternatively between about 180° C. and about 190° C., and alternatively between about 190° C. and about 200° C. The polymeric composite may also have the same melting point temperatures and temperature ranges as described above for the core polymer.

In order to produce such a color changeable polymeric composite, color changeable indicator particles such as those discussed above are combined with a second polymer (referred to as the bulk polymer herein) and extruded and/or melted as described, for example, herein. The second polymer (bulk polymer) and the polymer core from the color changeable indicator particles combine together during extrusion and/or melting to form the at least one organic polymer of the color changeable polymeric composite. The at least one color changeable indicator from the color changeable indicator particles becomes substantially homogenously dispersed within the at least one organic polymer.

The second or bulk polymer may be the same or different from the polymer used as the core polymer in the color changeable indicator particles. Both bulk and core polymers are meltable at generally low temperatures and have a melting point such that they are capable of being extruded and/or melted, for example, using known extrusion and/or melting techniques. Both the bulk and core polymers are preferably a solid at room temperature. The bulk and core polymer can have the same melting points or different melting points. The second or bulk polymer may have the same melting point temperatures and temperature ranges as described above for the core polymer. The second or bulk polymer may have the same melting points and melting point ranges as the core polymer as discussed above.

As described above, the bulk and core polymers can be, for example, low density polyethylene (LDPE), linear low density polyethylene (LLDPE), high density polyethylene (HDPE), isotactic polymethyl methacrylate (IPMMA), polymethyl methacrylate (PMMA), polystyrene (PS), polypropylene (PP), polyvinylidene fluoride (PVDF), polyoxymethylene (POMH), polybutene-1 (PB), nylon 11 (PA 11), nylon 12 (PA 12), ethylene-vinyl acetate (EVA), polycaprolactone (PCL), polyethylene oxide (PEOX), polypropylene oxide (PPDX) or mixtures thereof. Exemplary polymers and their melting points are listed in Table 1.

A color changeable composite, e.g. a film, is particularly useful as the color changeable layer of the present pressure sensitive color changeable indicators. As discussed above, the color changeable material is incorporated into the color changeable layer when a color changeable composite, e.g. film, is used.

Transition Layer

Applicant determined that use of an additional layer or layers between the reagent releasing layer and the color changeable layer and/or between multiple reagent releasing layers improves the functionality of the present pressure sensitive color changeable indicators. Specifically, Applicant determined that a transition layer between the reagent releasing layer and the color changeable layer and/or between two reagent releasing layers prevents premature reaction between the two layers and avoids or lessens the chances of false positive results, i.e. a premature inaccurate color change where the color changeable indicator has not been exposed to high pressure.

In one embodiment, the transition layer is a permeable membrane. For examples, the permeable membrane can be a water permeable membrane, such as filter paper, or track-etched membrane filters. The latter are typically made from polycarbonate and have well-defined or predetermined pore sizes, which provide greater control of the pressure needed to squeeze the water plus reactant from the reactant layer to the color-changeable layer. The water permeable membrane can be made of, for example, paper, nylon, PTFE and/or polycarbonate. The water permeable membrane can have a defined or predetermined pore size of about 0.01 to about 1 micron. Specifically, Applicants have determined that a water permeable membrane having pore size of about 0.01 to about 0.1 microns is particularly useful at lower pressure HPP (e.g., below about 400 MPa or about 200-400 MPa or about 300-400 MPa), preferably about 0.01 to about 0.05 microns, preferably about 0.03 microns. Applicants also determined that a water permeable membrane having a pore size of about 0.1 to about 1 micron is particularly useful at higher pressure HPP (e.g., above about 400 MPa or about 400-650 MPa or about 500-600 MPa), preferably about 0.2 to about 0.5 microns, preferably about 0.2 microns. The small pore size prevents premature color change of the indicator prior to exposure to high pressure.

In another embodiment, the transition layer is a permeable hydrated layer. The permeable hydrated layer can comprise, for example, a silica doped hydrated paper, or any water-laden (i.e. hydrated) desiccant, where the desiccant can be, for example, activated carbon, activated alumina, calcium sulfate, chloride or oxide, molecular sieves, and super absorbent polymers such as sodium polyacrylate. The permeable hydrated layer can comprise hydrated particles and binder particles. The binder particles can be, for example, paper and/or polymer binder particles. The hydrated particles can be, for example, the water-laden (i.e. hydrated) desiccants listed above. The hydrated particles are typically hydrated using distilled and/or deionized water. The hydrated particles are typically hydrated to about 60-80% by weight liquid, preferably about 65-75%, more preferably about 68-72%, most preferably about 70-71%. The hydrated particles, e.g. silica gel particles, can have a particle size of about 0.1 to about 1000 microns, preferably about 1 to about 100 microns, preferably about 1 to about 10 microns, preferably about 25 microns. Applicants have found that a permeable hydrated layer allows for among other things a simplified reagent releasing layer, e.g. one that only releases acid or base and not water. It also prevents premature color change of the indicator prior to exposure to high pressure.

In another embodiment, the transition layer is disposed between two reagent releasing layers to prevent reaction of the released reagents. In some embodiments such a transition layer is comprised of a permeable or non-permeable material with holes or voids. In this manner it can separates the two reagent releasing layers or tablets at standard or atmospheric pressure. Then, at high pressure, such a transition layer allows the two reagent releasing layers to contact and react with each other, thereby generating a product that changes the color of the indicator film. For example, in this case the two tablets might contain an acid and a bicarbonate, respectively, which when forced into physical contact together (due to a high pressure treatment) generate carbon dioxide which will change the color of a carbon dioxide sensitive plastic indicator film. Alternatively, the two opposing tablets may contain a base and an ammonium salt, respectively, which when forced into in physical contact together (due to a high pressure treatment) generate ammonia which will change the color of an ammonia sensitive plastic indicator film. A transition layer or layers may also separate more than two reagent releasing layers.

Figure 4:
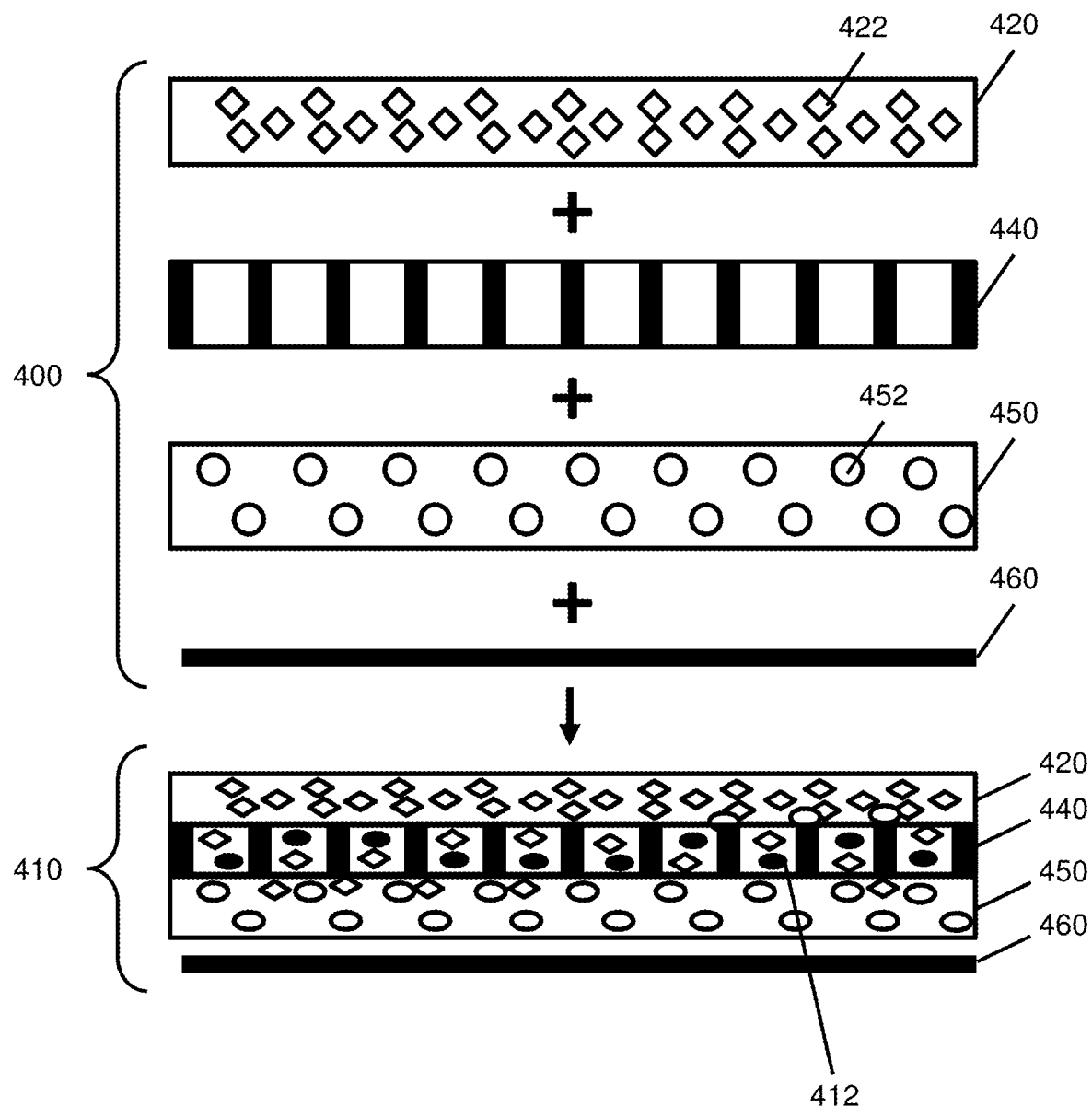
FIG. 4 shows an embodiment of the present color changeable HPP indicators that uses acid and sodium bicarbonate tablets (to cause the release of carbon dioxide), a perforated disc and a color changeable film.
Figure 12:
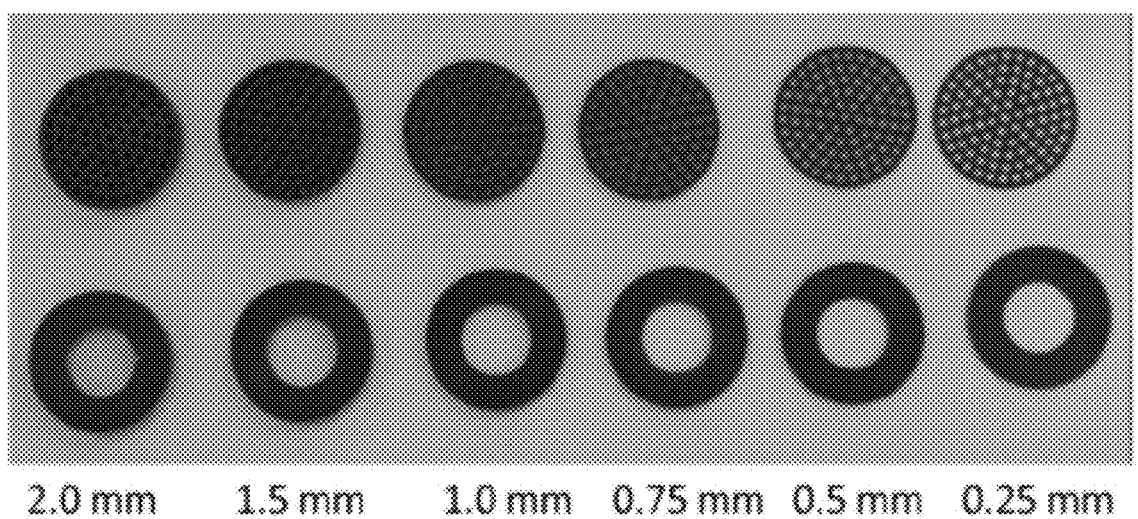
FIG. 12 shows non-porous washers and discs for use as transition layers in embodiments of the present pressure sensitive color changeable indicators.

A type of transition layer is used in the type of indicator illustrated in FIG. 4. This type of transition layer can be, for example, a washer, perforated disc, screen and/or mesh. FIG. 12 shows examples of washers and perforated discs of the present embodiment. The transition layer can be formed from an inert material, for example, Polyvinyl chloride (PVC), steel, plastic, nylon, polycarbonate, rubber, PTFE, silicone and/or paper. The washers can preferably have a bore of about 3 to about 10 mm in diameter, preferably about 5 to about 8 mm, more preferably about 7 to about 8 mm, preferably about 7.5 mm. The perforated discs, screens or mesh comprised of non-permeable material can preferably have a mesh size of about 0.1 to about 1 mm, preferably about 0.25 to about 0.75 mm, preferably about 0.5 mm. The non-permeable layer with holes or voids can be have a thickness of about 0.1 to about 10 mm, preferably about 0.25 to about 2 mm, or at least about 0.25 mm, at least about 0.5 mm, at least about 0.75 mm, at least about 1.0 mm, at least about 1.5 mm, at least about 2 mm, at least about 3 mm, at least about 4 mm, at least about 5 mm, at least about 6 mm and at least about 7 mm.

Protectant

Applicant determined that use of a protectant covering or encompassing the reagent releasing layer, transition layer and color changeable layer improves the functionality of certain types of the present pressure sensitive color changeable indicators. Specifically, Applicant determined that a protectant may prevent the indicator from drying out which can cause the pressure sensitive color changeable indicator to revert to its initial non-triggered color and present a false negative, i.e. the indicator would dry out and appear as though it had not been exposed to high pressure despite the fact that it has been exposed to high pressure. This allows color changeable indicators of the present invention without a protectant to be used for immediate review and analysis. However, the protectant allows the color changeable indicators to maintain their triggered state and be reviewed and analyzed at a later time without providing a false negative. The protectant also acts to protect the indicator from external contaminants and environmental conditions, e.g. acids, bases, water, etc., that could cause or prevent a color change resulting in inaccurate indication.

The protectant is impermeable to liquid and ion-migration. In some embodiments, it can be gas permeable. It some embodiments it is non-porous. Preferably it has a very low permeability to water vapor so that the indicators do not dry out. Preferably the protectant is made of a thermoplastic that is easily sealed using heat. Most polymers are ion-impermeable and gas permeable. As such, the protectant can be made out of, for example, low density polyethylene (LDPE), linear low density polyethylene (LLDPE), high density polyethylene (HDPE), PVC, polybenzimidazole, acrylonitrile butadiene styrene, polyether sulfone, polyether ether ketone, polyetherimide, polystyrene, polymethyl methacrylate (PMMA), PTFE, nylon, polycarbonate (PC), and/or PET. The protectant can be applied around the reagent releasing layer, transition layer and color changeable layer by, for example, vacuum sealing and/or heat sealing. In order to render the protectant largely water vapor impermeable, it is usually covered with a thin layer of aluminum or silicon oxide. Common polymers, used in the food packaging industry for example, with these coatings include PET and PE. In one embodiment, the protectant is made of a laminated film comprising polyamide and polyethylene layers. In another preferred embodiment, the protectant is made of aluminum oxide coated PET.

Additional Features

Additional components or layers can be included in the pressure sensitive color changeable indicator of the present technology. For example, an adhesive layer, e.g. a pressure sensitive adhesive, could be disposed on an outermost layer of the present color changeable indicators. In this manner, the color changeable indicator could easily be affixed to the product or packaging undergoing HPP processing like a sticker. As another example, the bottom layer, e.g. one of the reagent releasing layers or the protectant, can be disposed on a substrate. The substrate can offer strength and support to the color changeable indicator.

At least a portion of the color changeable layer changes color upon exposure of the indicator to high pressure including high pressure pasteurization and high hydrostatic pressures associated with high pressure pasteurization. Specifically, at least a portion of the color changeable layer changes color upon exposure of the indicator to at least about 250 MPa of pressure, at least about 300 MPa of pressure, at least about 350 MPa of pressure, at least about 400 MPa of pressure, at least about 450 MPa of pressure, at least about 500 MPa of pressure, at least about 525 MPa of pressure, at least about 550 MPa of pressure, at least about 600 MPa of pressure. In one embodiment, at least a portion of the color changeable layer changes color immediately upon exposure of the indicator to at least about 250 MPa of pressure, at least about 300 MPa of pressure, at least about 350 MPa of pressure, at least about 400 MPa of pressure, at least about 450 MPa of pressure, at least about 500 MPa of pressure, at least about 525 MPa of pressure, at least about 550 MPa of pressure, at least about 600 MPa of pressure.

In another embodiment, at least a portion of the color changeable layer changes color after exposure of the indicator to a defined or predetermined amount of pressure for a defined or predetermined period of time. For example, the defined or predetermined amount of pressure can be about 200 to about 650 MPa, about 200 to about 300 MPa, about 300 to about 400 MPa, or about 400 to about 500 MPa, about 500 to about 600 MPa. As another example, the defined or predetermined amount of pressure can be at least about 250 MPa of pressure, at least about 300 MPa of pressure, at least about 350 MPa of pressure, at least about 400 MPa of pressure, at least about 450 MPa of pressure, at least about 500 MPa of pressure, at least about 525 MPa of pressure, at least about 550 MPa of pressure, at least about 600 MPa of pressure. For example, the defined or predetermined amount of time can be about 15 to 30 seconds, 30 seconds to a minute, 1 to 5 minutes, 5 to 10 minutes, about 10 minutes, greater than 10 minutes. The delay of color change of at least a portion of the color changeable layer can be achieved, for example, by having a transition layer that is a permeable membrane having a certain pore size and the defined or predetermined period of time is controlled adjusting the pore size of the permeable membrane, e.g. by making the pores larger the time of color change can be shortened.

The present technology is particularly useful in the food, beverage, pharmaceutical and medical device areas. However, it is not limited to such uses. The present indicators can be used directly on a product, e.g. a sticker or label directly on a food product or medical device. The present indicators can also be used on the packaging of a product, e.g. an indicator applied to or incorporated into the product packaging. The present indicators can also be used with large amounts of product, e.g. pallets of product in production and shipping facilities. For example, indicators may be placed in one or multiple places on a pallet of product to determine whether the whole pallet of product has been exposed to high pressure.

In some embodiments, multiple color changeable indicators of the present technology can be used together on one product, packaging or apparatus. For example, a lower pressure HPP color changeable indicator (e.g., one that changes color in response to exposure to pressures between about 200 and 300 MPa) and a higher pressure HPP color changeable indicator (e.g., one that changes color in response to exposure to pressures between about 500 and 600 MPa) could both be applied to a product, packaging or apparatus. This would allow the user to know that the product was exposed to lower pressure HPP but not to higher pressure HPP. In another example, a color changeable indicator that changes color after a short amount of exposure to pressure (e.g. one that changes after 0-10 seconds of exposure to a certain amount of pressure) and a color changeable indicator that changes color after a long amount of exposure to pressure (e.g. one that changes after 10 minutes of exposure to a certain amount of pressure) could both be applied to a product, packaging or apparatus. This would allow the user to know that the product had been exposure to a certain amount of pressure for a short or long amount of time.

Embodiments

Figure 2:
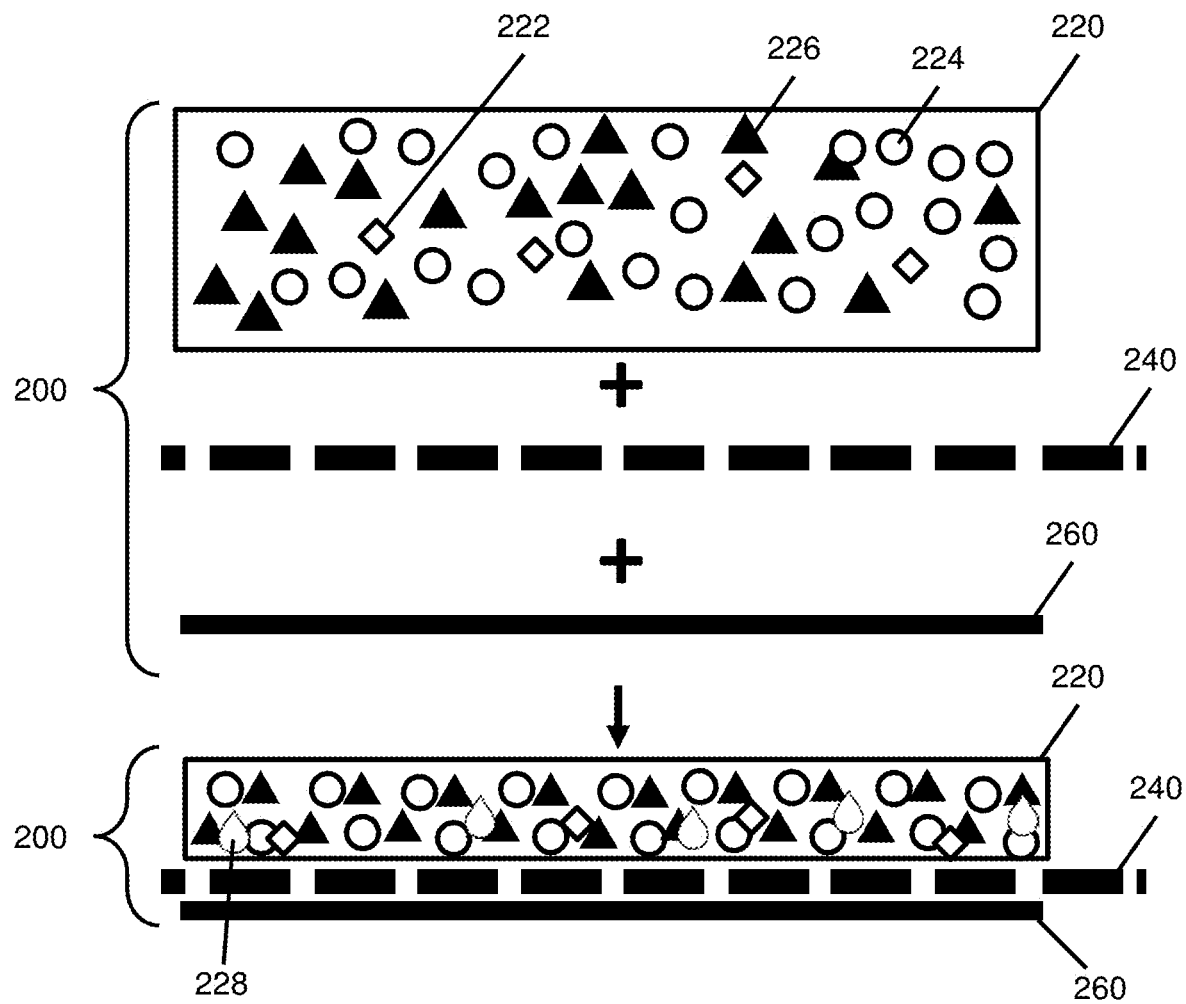
FIG. 2 shows an embodiment of the present color changeable HPP indicators that uses an acid and water releasing tablet, a water permeable membrane and a color changeable film.

FIG. 2 shows a schematic representation of one embodiment of the present pressure sensitive color changeable indicators before exposure to high pressure 200 and in its triggered state (after exposure to high pressure, e.g., 600 MPa for 10 minutes) 210. The pressure sensitive color changeable indicator comprises an acid and water releasing layer (e.g. a tablet) 220, a water permeable membrane 240 which is a transition layer, a pH sensitive color changeable layer (e.g. a color changeable film) 260, and a protectant (not shown). In another embodiment, a base and water releasing layer (e.g. a tablet) could be substituted for the acid and water releasing layer.

In this embodiment, the acid and water releasing layer, e.g. tablet, 220 is made up of an organic acid 222, hydrated particles 224, and polymer binder particles 226. The three components are combined and compressed in a die or press to form a solid tablet.

The acid 222 can be, for example, camphor sulfonic acid (CPA), benzene sulfonic acid, sulfanilic acid, toluene sulfonic acid (TSA), and/or perfluorooctanoic acid. If a base is used in a base and water releasing layer, e.g. tablet, the base can be any hydroxide, bicarbonate or carbonate, for example, sodium hydroxide, sodium bicarbonate and/or sodium carbonate. The base can also be hydroxide, bicarbonate, carbonate salts of quaternary cations such as benzyltrimethyl ammonium, trioctylmethyl ammonium, tricaprylmethyl ammonium, tetraoctyl ammonium, tetrabutyl ammonium, cetyltrimethyl ammonium, tetrahexyl ammonium, tetraphenyl phosphonium, trioctyl phosphonium and/or hexadecyl tributyl phosphonium.

The hydrated particles 224 can be any powder material that can function as a desiccant, for example, silica gel, activated carbon, activated alumina, calcium sulfate, calcium chloride, molecular sieves, and/or super absorbent polymers, such as sodium polyacrylate. The hydrated particles 224 are typically hydrated using distilled and/or deionized water. The hydrated particles 224, e.g. silica gel particles, are preferably hydrated to about 60-80% by weight, preferably about 65-75%, more preferably about 68-72%, most preferably about 70-71%. The hydrated particles 224, e.g. silica gel particles, preferably have a particle size of at least about 1 micron.

The polymer 226 can be, for example, polycaprolactone, polytetrafluoro ethylene, polyvinyl alcohol, hydroxyl ethyl cellulose, polyethylene oxide, polyethylene, low density polyethylene, polylactide, poly vinyl pyridine and/or cellulose nitrate. The polymer binder particles 226 have a particle size of at least about 1 micron.

The water permeable membrane 240 can comprise, for example, filter paper, or track-etched membrane filters. The latter are typically made from polycarbonate and have well-defined pore sizes, which provide greater control of the pressure needed to squeeze the water plus reactant from the reactant layer to the color-changeable layer. The water permeable membrane 240 can be made of, for example, paper, nylon, PTFE and/or polycarbonate. The water permeable membrane 240 can have a defined or predetermined pore size of about 0.01 to about 1 micron. Specifically, the water permeable membrane can have a pore size of about 0.01 to about 0.1 microns for use with lower pressure HPP (e.g., below about 400 MPa or about 200-400 MPa or about 300-400 MPa), preferably about 0.01 to about 0.05 microns, preferably about 0.03 microns. In another embodiment, the water permeable membrane can have a pore size of about 0.1 to about 1 micron for use with higher pressure HPP (e.g., above about 400 MPa or about 400-650 MPa or about 500-600 MPa), preferably about 0.2 to about 0.5 microns, preferably about 0.2 microns.

FIG. 2 shows that when this embodiment of the present pressure sensitive color changeable indicator before exposure to high pressure 200 the color changeable layer 260 is not in contact with the acid (or base) 222 from the reagent releasing layer 220. As such, the color changeable material on or in the color changeable layer 260 is in its non-triggered state and first color. When the color changeable indicator is exposed to high pressure, it is changed to its triggered state 210. In the triggered state, the high pressure causes the reagent releasing layer 220 to release acid (or base) 222 and water 228. The acid (or base) 222 and water 228 pass through the water permeable membrane 240 and contact the color changeable layer (e.g. pH sensitive color changeable film) 260. The acid (or base) 222 and water 228 cause the pH sensitive color changeable material on or in the color changeable layer 260 to change to the triggered state and second color.

Figure 3:
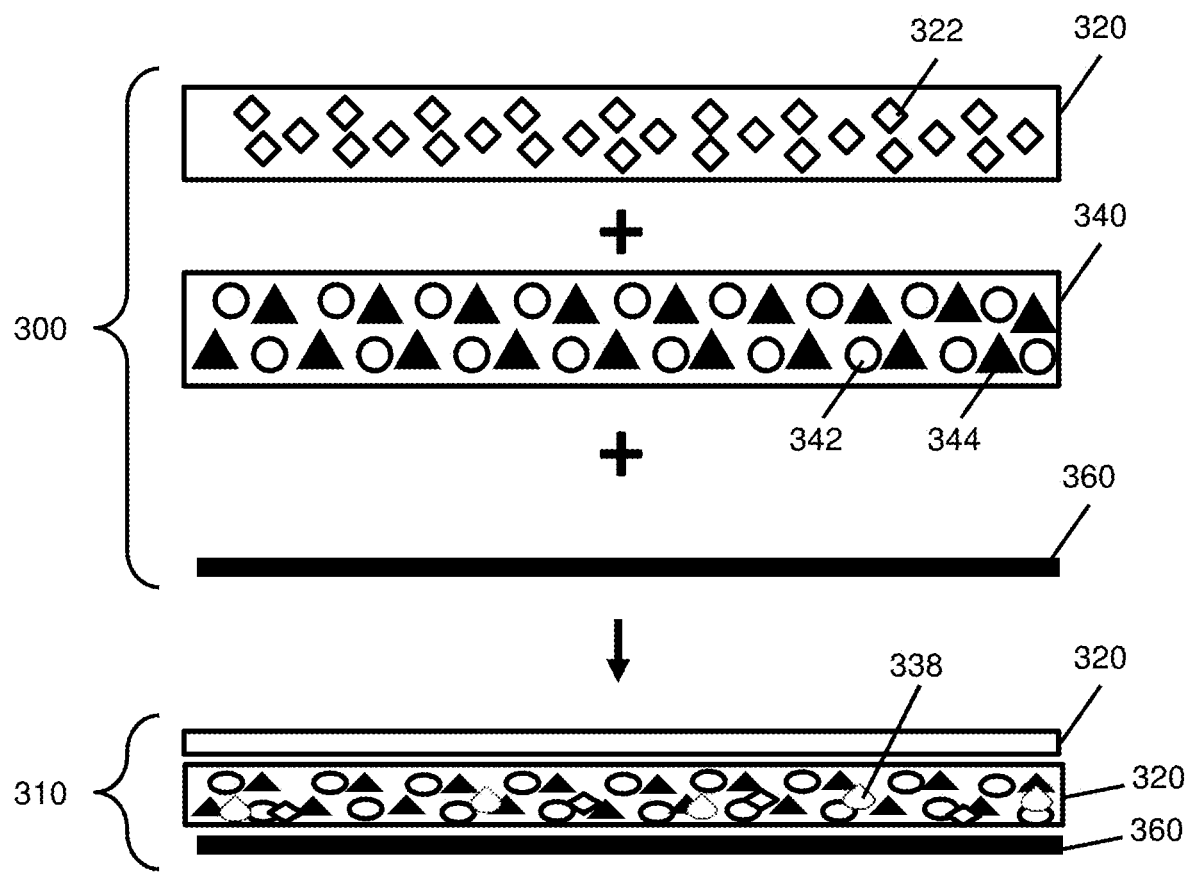
FIG. 3 shows an embodiment of the present color changeable HPP indicators that uses an acid releasing tablet, a silica doped hydrated layer and a color changeable film.

FIG. 3 shows one embodiment of the present pressure sensitive color changeable indicators before exposure to high pressure 300 and in its triggered state (after exposure to high pressure, e.g., 600 MPa for 10 minutes) 310. The pressure sensitive color changeable indicator comprises an acid releasing layer (e.g. a tablet) 320, a permeable hydrated layer 340 which is a transition layer, a pH sensitive color changeable layer (e.g. a film) 360, and a protectant (not shown). In another embodiment, a base releasing layer (e.g. a tablet) could be substituted for the acid releasing layer.

In this embodiment, the acid releasing layer, e.g. tablet, 320 comprises acid 322 that is compressed in a die or press to form a solid tablet. The acid 322 can be, for example, camphor sulfonic acid (CPA), benzene sulfonic acid, sulfanilic acid, toluene sulfonic acid (TSA), and/or perfluorooctanoic acid. If a base is used in a base releasing layer, e.g., tablet, the base can be any hydroxide, bicarbonate or carbonate, for example, sodium hydroxide, sodium bicarbonate and/or sodium carbonate. The base can also be hydroxide, bicarbonate, carbonate salts of quaternary cations such as benzyltrimethyl ammonium, trioctylmethyl ammonium, tricaprylmethyl ammonium, tetraoctyl ammonium, tetrabutyl ammonium, cetyltrimethyl ammonium, tetrahexyl ammonium, tetraphenyl phosphonium, trioctyl phosphonium and/or hexadecyl tributyl phosphonium.

The permeable hydrated layer 340 can be, for example, a silica doped hydrated paper layer, or any water-laden (i.e. hydrated) desiccant layer, where the desiccant can be: activated carbon, activated alumina, calcium sulfate, chloride or oxide, molecular sieves, and super absorbent polymers, such as sodium polyacrylate. The permeable hydrated layer 340 can comprise hydrated particles 342 and binder particles 344. The binder particles 344 can be, for example, paper and/or polymer binder particles. The hydrated particles 342 can be, for example, water-laden (i.e. hydrated) silica gel, activated carbon, activated alumina, calcium sulfate, chloride or oxide, molecular sieves, and super absorbent polymers, such as sodium polyacrylate particles. The hydrated particles 342 are typically hydrated using distilled and/or deionized water 60-80% by weight, preferably about 65-75%, more preferably about 68-72%, most preferably about 70-71%. The hydrated particles 342, e.g. silica gel particles, can have a particle size of about 0.1 to about 1000 microns, preferably about 1 to about 100 microns, preferably about 1 to about 10 microns, preferably about 25 microns.

FIG. 3 shows that when this embodiment of the present pressure sensitive color changeable indicator before exposure to high pressure 300 the color changeable layer 360 is not in contact with the acid (or base) 322 from the reagent releasing layer 320. As such, the color changeable material on or in the color changeable layer 360 is in its non-triggered state and first color. When the color changeable indicator is exposed to high pressure, it is changed to its triggered state 310. In the triggered state, the high pressure causes the reagent releasing layer 320 to release acid (or base) 222 and causes the permeable hydrated layer to release water 338. The acid (or base) 322 and water 338 pass through the permeable hydrated layer 340 and contact the color changeable layer (e.g. pH sensitive color changeable film) 360. The acid (or base) 322 and water 338 cause the pH color changeable material on or in the color changeable layer 360 to change to the triggered state and second color.

FIG. 4 shows one embodiment of the present pressure sensitive color changeable indicators before exposure to high pressure 400 and in its triggered state (after exposure to high pressure) 410. The pressure sensitive color changeable indicator comprises an acid releasing layer (e.g. a tablet) 420, a non-permeable transition layer with holes or voids (e.g. a washer, perforated disc, screen or mesh) 440, a base releasing layer (e.g. a tablet) 450, a pH sensitive (e.g. carbon dioxide sensing) color changeable layer (e.g. a film) 460, and a protectant (not shown).

In this embodiment, the acid releasing layer, e.g. tablet, 420 comprises acid 422 that is compressed in a die or press to form a solid tablet. The acid 422 can be, for example, camphor sulfonic acid (CPA), benzene sulfonic acid, sulfanilic acid, toluene sulfonic acid (TSA), and/or perfluorooctanoic acid.

In this embodiment, the base releasing layer, e.g. tablet, 450 comprises base 452 that is compressed in a die or press to form a solid tablet. The base can be, for example, any hydroxide, bicarbonate or carbonate, for example, sodium hydroxide, sodium bicarbonate and/or sodium carbonate. The base can also be hydroxide, bicarbonate, carbonate salts of quaternary cations such as benzyltrimethyl ammonium, trioctylmethyl ammonium, tricaprylmethyl ammonium, tetraoctyl ammonium, tetrabutyl ammonium, cetyltrimethyl ammonium, tetrahexyl ammonium, tetraphenyl phosphonium, trioctyl phosphonium and/or hexadecyl tributyl phosphonium.

In this embodiment, the transition layer 440 is a non-permeable layer with holes or voids which separates two reactant layers or tablets at standard pressure, but which at high pressure allows these two layers to contact and react with each other, thereby generating a product that changes the color of the indicator film. The non-permeable layer 440 can be, for example, a washer, perforated disc, screen and/or mesh. FIG. 12 shows examples of washers and perforated discs of the present embodiment. The non-permeable layer 440 can be formed from an inert material, for example, Polyvinyl chloride (PVC), steel, plastic, nylon, polycarbonate, rubber, PTFE, silicone and/or paper. The washers can preferably have a bore of about 3 to about 10 mm in diameter, preferably about 5 to about 8 mm, more preferably about 7 to about 8 mm, preferably about 7.5 mm. The perforated discs, screens or mesh comprised of non-permeable material can preferably have a mesh size of about 0.1 to about 1 mm, preferably about 0.25 to about 0.75 mm, preferably about 0.5 mm. The non-permeable layer with holes or voids can be have a thickness of about 0.1 to about 10 mm, preferably about 0.25 to about 2 mm, or at least about 0.25 mm, at least about 0.5 mm, at least about 0.75 mm, at least about 1.0 mm, at least about 1.5 mm, at least about 2 mm, at least about 3 mm, at least about 4 mm, at least about 5 mm, at least about 6 mm and at least about 7 mm.

FIG. 4 shows that when this embodiment of the present pressure sensitive color changeable indicator before exposure to high pressure 400 the color changeable layer 460 is not in contact with the reaction product (carbon dioxide) of the acid 422 or base 452 from the acid releasing layer (e.g. tablet) 420 and base releasing layer (e.g. tablet) 450. As such, the color changeable material on or in the color changeable layer 460 is in its non-triggered state and first color. When the color changeable indicator is exposed to high pressure, it is changed to its triggered state 410. In the triggered state, the high pressure causes the acid releasing layer 420 to release acid 422 and the base releasing layer 450 to release base 452. The acid 422 and base 452 pass through the holes 442 in the non-porous layer 440 and react with each other to form a reaction product of carbon dioxide 412. The carbon dioxide 412 contacts the color changeable layer (e.g. pH sensitive, carbon dioxide sensing color changeable film) 460. The carbon dioxide 412 causes the color changeable material on or in the color changeable layer 460 to change to the triggered state and second color.

The present color changeable indicators can change color when exposed to high pressure. Specifically, at least a portion of the color changeable layer changes color upon exposure of the indicator to at least about 250 MPa of pressure, at least about 300 MPa of pressure, at least about 350 MPa of pressure, at least about 400 MPa of pressure, at least about 450 MPa of pressure, at least about 500 MPa of pressure, at least about 525 MPa of pressure, at least about 550 MPa of pressure, at least about 600 MPa of pressure. In one embodiment, at least a portion of the color changeable layer changes color immediately upon exposure of the indicator to at least about 250 MPa of pressure, at least about 300 MPa of pressure, at least about 350 MPa of pressure, at least about 400 MPa of pressure, at least about 450 MPa of pressure, at least about 500 MPa of pressure, at least about 525 MPa of pressure, at least about 550 MPa of pressure, at least about 600 MPa of pressure.

Alternatively, at least a portion of the color changeable layer changes color after exposure of the indicator to a defined or predetermined amount of pressure for a defined or predetermined period of time. For example, the defined or predetermined amount of pressure can be about 200 to about 650 MPa, about 200 to about 300 MPa, about 300 to about 400 MPa, or about 400 to about 500 MPa, about 500 to about 600 MPa. As another example, the defined or predetermined amount of pressure can be at least about 250 MPa of pressure, at least about 300 MPa of pressure, at least about 350 MPa of pressure, at least about 400 MPa of pressure, at least about 450 MPa of pressure, at least about 500 MPa of pressure, at least about 525 MPa of pressure, at least about 550 MPa of pressure, at least about 600 MPa of pressure. For example, the defined or predetermined amount of time can be about 15 to 30 seconds, 30 seconds to a minute, 1 to 5 minutes, 5 to 10 minutes, greater than 10 minutes. The delay of color change of at least a portion of the color changeable layer can be achieved, for example, by having a transition layer that is a permeable membrane having a certain pore size and the defined or predetermined period of time is controlled adjusting the pore size of the permeable membrane, e.g. by making the pores larger the time of color change can be shortened.

Method of Manufacturing

The present pressure sensitive color changeable indicators are manufactured by (1) producing one or more reagent releasing layer(s), (2) disposing a transition layer disposed on said reagent releasing layer, (3) producing a color changeable layer, (4) disposing said color changeable layer on said transition layer, and (5) optionally applying a protectant to encompass the reagent releasing layer(s), transition layer and color changeable layer.

As discussed above, the reagent releasing layer in the form of a reagent releasing tablet can be produced, for example, by compressing an acid or base using a die or press. The reagent releasing layer can be any of the variations and have any of the qualities discussed above in the Reagent Releasing Layer section.

The transition layer can be disposed on the reagent releasing layer. In some embodiments it can be affixed to the reagent releasing layer, e.g. using an adhesive or other affixation techniques known in the technology. The transition layer can be any of the variations and have any of the qualities discussed above in the Transition Layer section.

As discussed above the color changeable layer can be in the form of a color changeable polymeric composite film produced by the methods of U.S. patent application Ser. No. 15/832,379 (incorporated herein in its entirety). In order to produce such a color changeable polymeric composite film, color changeable indicator particles such as those discussed above are combined with a second polymer (referred to as the bulk polymer herein) and extruded and/or melted. The color changeable layer can be any of the variations and have any of the qualities discussed above in the Color Changeable Layer section.

The protectant can be applied to encompass the reagent releasing layer(s), transition layer and color changeable layer. As discussed above, the protectant can be applied around the reagent releasing layer(s), transition layer and color changeable layer by, for example, vacuum sealing and/or heat sealing. The protectant can be any of the variations and have any of the qualities discussed above in the Protectant section.

In some embodiments a second reagent releasing layer can be disposed between the transition layer and color changeable layer.

As discussed above, additional components or layers can be included in the pressure sensitive color changeable indicator of the present technology. For example, an adhesive layer, e.g. a pressure sensitive adhesive, could be disposed on an outermost layer (e.g., the protective layer or a reagent releasing layer) of the present color changeable indicators. In this manner, the color changeable indicator could easily be affixed to the product or packaging undergoing HPP processing like a sticker. As another example, the bottom layer, e.g. one of the reagent releasing layers or the protectant, can be disposed on a substrate. The substrate can offer strength and support to the color changeable indicator. For example, the pressure sensitive color changeable indicator can be attached to the substrate with an adhesive, e.g. a pressure sensitive adhesive, a hot-melt adhesive, etc. In some embodiments, the substrate can be the product or packaging itself and the pressure sensitive color changeable indicator can be applied to it, e.g. as a label.

Example 1

An acid and water releasing tablet is prepared by adding 40 mg of solid organic acid (CPA), 1 g of hydrated silica gel (hydrated to 70%, 75% or 80% with distilled deionized water) and 500 mg of powdered polycaprolactone. A tablet is prepared in a press or die (1.0 T/10 seconds) using 500 mg of the resulting mixture.

A Congo Red pH sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. Discs of 13 mm in diameter are then cut out of the film.

The color changeable film discs are placed on the acid and water releasing tablet in some samples. In other samples, a water permeable membrane made of polycarbonate having a pore size of 0.2 microns is placed between the color changeable film and the acid and water releasing tablet.

The tablets with the color changeable films and with or without the membranes are vacuum sealed in a protectant made of aluminum oxide coated PET to form the pressure sensitive color changeable indicators.

Figure 5:
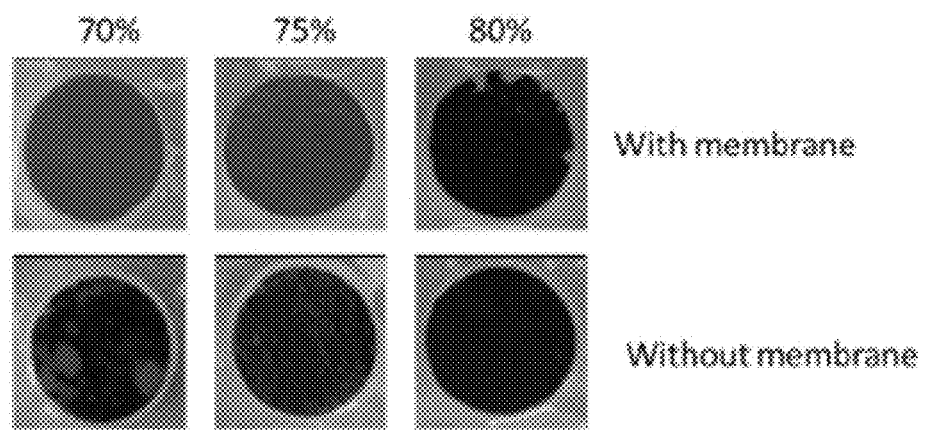
FIGS. 5-11 show photographs of various pressure sensitive color changeable indicators of the present technology.

FIG. 5 shows the resulting color changeable indicators prior to exposure to high pressure to simulate HPP. The reddish/orange color is the initial color of the Congo Red film prior to exposure of the film to acid from the acid and water releasing tablet. The bluish/black color is the triggered color of the Congo Red film after exposure of the film to acid from the acid and water releasing tablet. The samples without the membrane all show color change of the Congo Red film prior to exposure of the indicator to pressure (600 MPa) to simulate HPP. The 80% hydrated silica gel also shows color change of the Congo Red film prior to exposure of the indicator to high pressure to simulate HPP. The 70% and 75% hydrated silica gel samples with the membrane perform favorably and do not show color change of the Congo Red film prior to exposure of the indicator to high pressure to simulate HPP.

Example 2

An acid and water releasing tablet is prepared by adding 40 mg of solid organic acid (CPA), 1 g of hydrated silica gel (hydrated to 70-75% with distilled deionized water) and 500 mg of powdered polycaprolactone. A tablet is prepared in a press or die (1.0 T/10 seconds) using 500 mg of the resulting mixture.

A Congo Red pH sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. Discs of 13 mm in diameter are then cut out of the film.

The color changeable film discs are placed on a water permeable membrane made of polycarbonate having a pore size of 0.2 microns. The acid and water releasing tablet is placed the opposite side of the water permeable membrane from the color changeable film.

The tablets, membranes and color changeable films are vacuum sealed in two types of protectants to form the pressure sensitive color changeable indicators. The first protectant is made of a laminated film comprising polyamide and polyethylene layers. The second protectant is made of aluminum oxide coated PET.

The indicators are exposed to hydrostatic pressure of 600 MPa for 10 minutes to simulate HPP.

Figure 6:
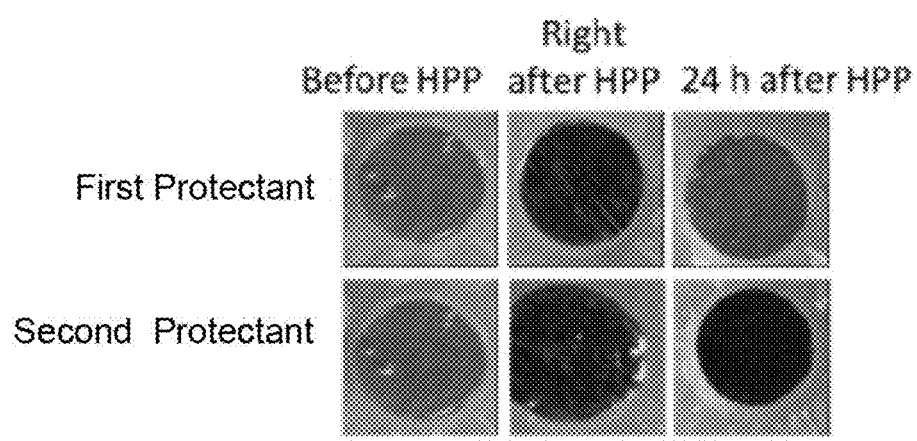

FIG. 6 shows the resulting color changeable indicators prior to exposure to high pressure to simulate HPP, right after exposure to high pressure and 24 hours after exposure to high pressure. The reddish/orange color is the initial color of the Congo Red film prior to exposure of the film to acid from the acid and water releasing tablet. The bluish/black color is the triggered color of the Congo Red film after exposure of the film to acid from the acid and water releasing tablet. Both samples show the desired reddish/orange color prior to exposure of the indicator to high pressure to simulate HPP. Both samples show the desired bluish/black color after exposure of the indicator to high pressure to simulate HPP. However, the first protectant reverts back to the original reddish/orange color 24 hours after exposure to high pressure to simulate HPP. The second protectant performs favorably and retains the bluish/black color 24 hours after exposure to high pressure to simulate HPP.

Example 3

An acid and water releasing tablet is prepared by adding 40 mg of solid organic acid (CPA), 1 g of hydrated silica gel (hydrated to 75% with distilled deionized water) and 500 mg of powdered polycaprolactone. A tablet is prepared in a press or die (1.0 T/10 seconds) using 500 mg of the resulting mixture.

A Congo Red pH sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. Discs of 13 mm in diameter are then cut out of the film.

The color changeable film discs are placed on a water permeable membrane made of polycarbonate having a pore size of 0.03 microns. The acid and water releasing tablet is placed the opposite side of the water permeable membrane from the color changeable film.

The tablets, membranes and color changeable films are vacuum sealed in a protectant made of aluminum oxide coated PET to form the pressure sensitive color changeable indicators.

The indicators are then allowed to age for 0, 1, 3, 5 7, and 12 weeks. After aging they are exposed to hydrostatic pressure of 600 MPa for 10 minutes to simulate HPP.

Figure 7:
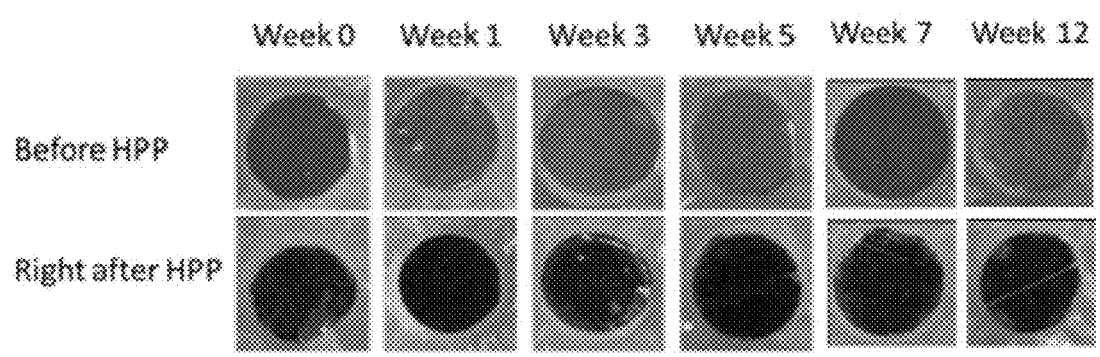

FIG. 7 shows the resulting color changeable indicators of different ages prior to exposure to high pressure to simulate HPP and right after exposure to high pressure. The reddish/orange color is the initial color of the Congo Red film prior to exposure of the film to acid from the acid and water releasing tablet. The bluish/black color is the triggered color of the Congo Red film after exposure of the film to acid from the acid and water releasing tablet. All samples show the desired reddish/orange color prior to exposure of the indicator to high pressure to simulate HPP. All samples show the desired bluish/black color after exposure of the indicator to high pressure to simulate HPP.

Example 4

An acid and water releasing tablet is prepared by adding 40 mg of solid organic acid (CPA), 1 g of hydrated silica gel (hydrated to 75% with distilled deionized water) and 500 mg of powdered polycaprolactone. A tablet is prepared in a press or die (1.0 T/10 seconds) using 500 mg of the resulting mixture.

A Congo Red pH sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. Discs of 13 mm in diameter are then cut out of the film.

The color changeable film discs are placed on one of three water permeable membrane: (1) one made of polycarbonate having a pore size of 0.03 microns, (2) one made of polycarbonate having a pore size of 0.2 microns, and (3) silicon doped paper. The acid and water releasing tablet is placed the opposite side of the water permeable membrane from the color changeable film.

The tablets, membranes and color changeable films are vacuum sealed in a protectant made of aluminum oxide coated PET to form the pressure sensitive color changeable indicators.

The indicators are then exposed to hydrostatic pressure of 600, 525, 450, or 300 MPa for 10 minutes to simulate HPP.

Figure 8:
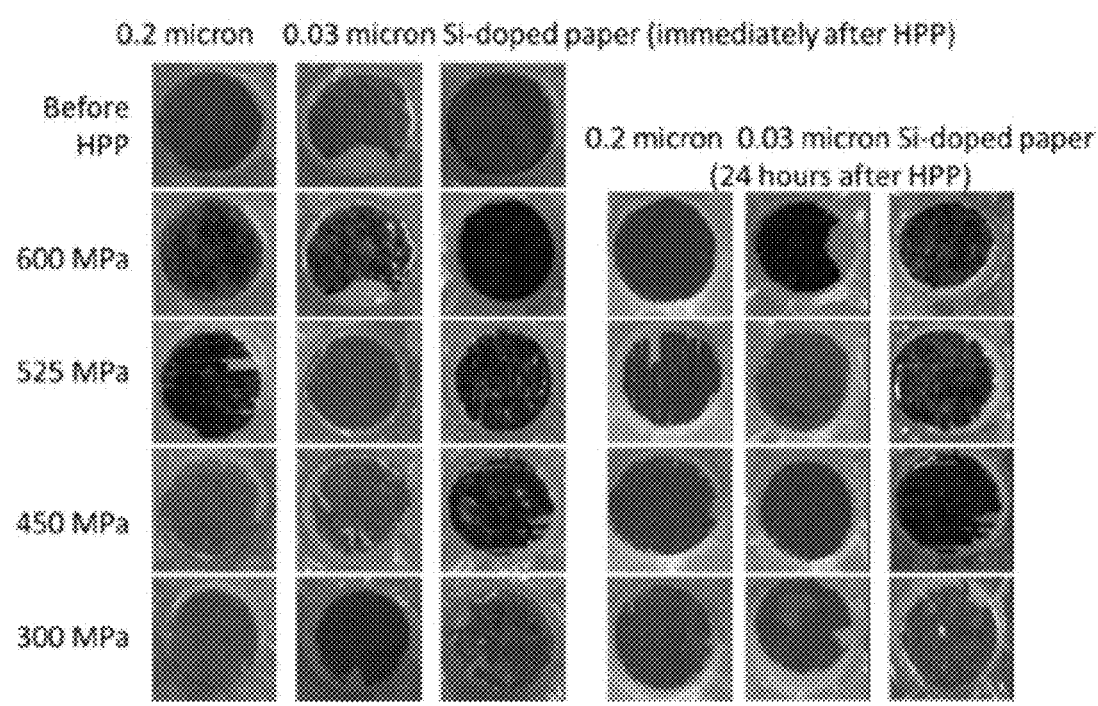

FIG. 8 shows the resulting color changeable indicators with different water permeable membranes and at different pressures. Results are shown prior to exposure to high pressure to simulate HPP, right after exposure to high pressure and 24 hours after exposure to high pressure. The reddish/orange color is the initial color of the Congo Red film prior to exposure of the film to acid from the acid and water releasing tablet. The bluish/black color is the triggered color of the Congo Red film after exposure of the film to acid from the acid and water releasing tablet. All samples show the desired reddish/orange color prior to exposure of the indicator to high pressure to simulate HPP. None of the samples show the desired color change to bluish/black immediately after exposure to 300 MPa. All of the samples show some color change to bluish/black immediately after exposure to 600 MPa. The 0.2 micron membrane also shows the bluish/black color change immediately after exposure to 525 MPa. The Silica gel doped paper also shows the bluish/black color change immediately after exposure to 525 and 450 MPa. Only the 0.03 micron membrane and the Silica gel doped paper maintain the bluish/black color as desired 24 hours after exposure to high pressure (600 MPa and 450, 525, and 600 MPa respectively).

Example 5

An acid releasing tablet is prepared by pressing 500 mg of solid organic acid (toluene sulfonic acid) in a 13 mm die (5.0 T/10 seconds).

A Congo Red pH sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. Discs of 13 mm in diameter are then cut out of the film.

Silica gel doped paper which is ca. 2.5 mm thick, containing 40% silica gel is cut into 13 mm circles using a cutting die tool. The paper is wetted (with distilled deionized water) with a micro syringe (to ~5.8-6.9% water content).

The color changeable film is placed on the hydrated Silica gel doped paper. The acid releasing tablet is placed the opposite side of the hydrated Silica gel doped paper from the color changeable film.

The tablets, hydrated Silica gel doped paper and color changeable films are vacuum sealed in a protectant made of aluminum oxide coated PET to form the pressure sensitive color changeable indicators.

The indicators are then allowed to age for 0, 1, 3, 5 7, and 12 weeks. After aging they are exposed to hydrostatic pressure of 550 MPa for 10 minutes to simulate HPP.

Figure 9:
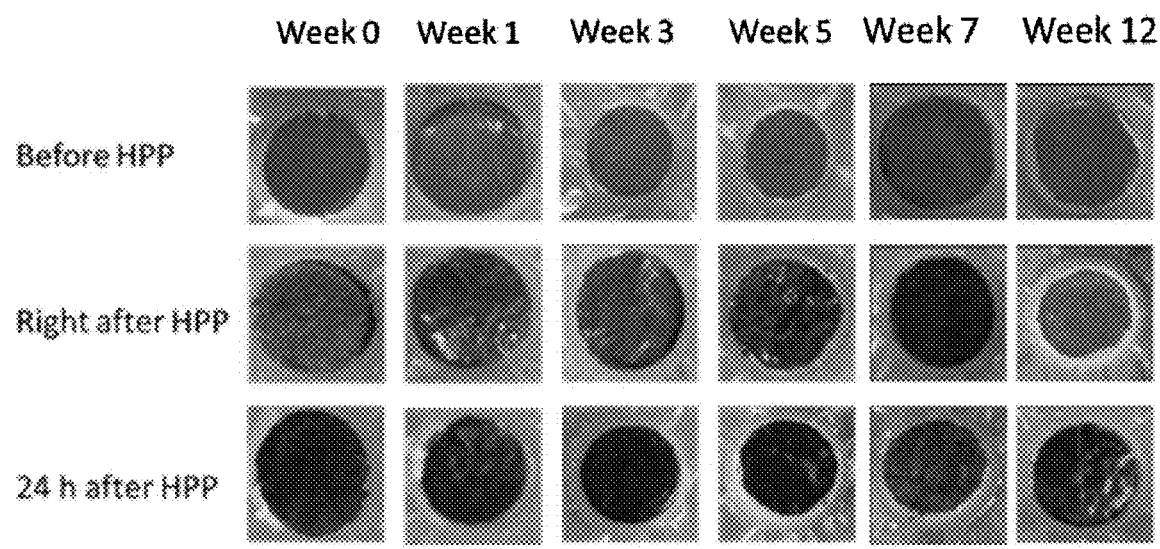

FIG. 9 shows the resulting color changeable indicators of different ages and with different water contents prior to exposure to high pressure to simulate HPP, right after exposure to high pressure and 24 hours after exposure to high pressure. The reddish/orange color is the initial color of the Congo Red film prior to exposure of the film to acid from the acid and water releasing tablet. The bluish/black color is the triggered color of the Congo Red film after exposure of the film to acid from the acid and water releasing tablet. All samples show the desired reddish/orange color prior to exposure of the indicator to high pressure to simulate HPP. All samples show at least a small amount of the desired bluish/black color immediately after exposure of the indicator to high pressure to simulate HPP. The indicators perform favorably and retain their bluish/black color 24 hours after exposure to high pressure to simulate HPP.

Example 6

An acid releasing tablet is prepared by pressing 500 mg of solid organic acid (toluene sulfonic acid) in a 13 mm die (5.0 T/10 seconds).

A base releasing tablet is prepared by pressing 500 mg of solid base (sodium bicarbonate) in a 13 mm die (5.0 T/10 seconds).

A 10% Metacresol Purple (MCP) and Ethylene vinyl acetate (EVA) pH/carbon dioxide sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. The film is a very deep blue color that changes to yellow in excess of carbon dioxide. This film is cut to circles 13 mm in diameter.

The three layers are assembled with the acid releasing tablet on the bottom, the base releasing tablet on top of the acid releasing tablet and the color changeable film on top of the base releasing layer. Different transition layers are inserted between the acid releasing layer and base releasing layer in some samples—filter paper, Silica gel doped paper, punctured PET film and a 0.2 micron porous membrane made of polycarbonate.

The tablets, transition layer (if included) and color changeable films are vacuum sealed in a protectant made of aluminum oxide or silicon oxide coated thermoplastic films, such as PET to form the pressure sensitive color changeable indicators.

The indicators are then aged for three days and exposed to hydrostatic pressure of 600 MPa for 10 minutes to simulate HPP.

Figure 10:
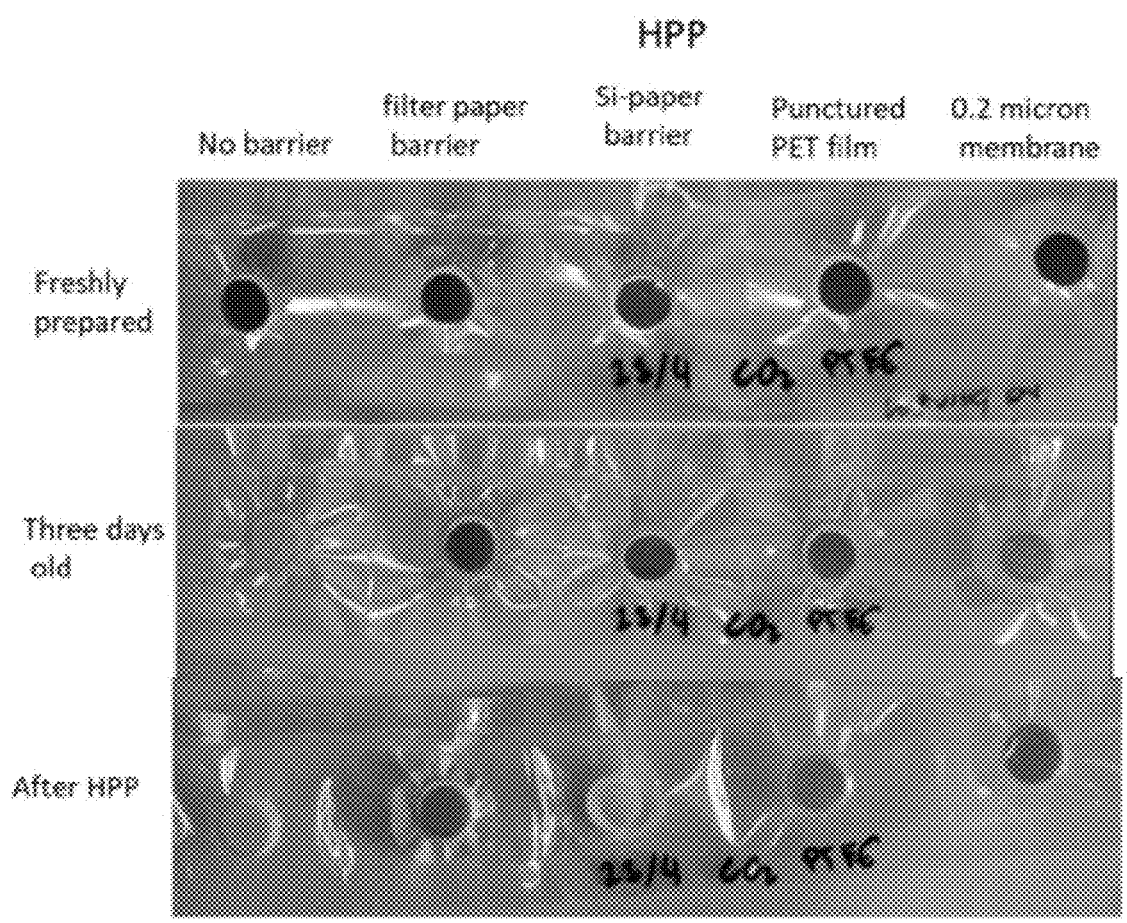

FIG. 10 shows the resulting color changeable indicators with different transition layers immediately after being prepared, after aging for three days and after exposure to high pressure. The bluish color is the initial color of the MCP film prior to exposure of the film to higher carbon dioxide from reaction of the acid and base from the releasing tablets. The yellowish/green color is the triggered color of the MCP film after exposure of the film to carbon dioxide from the reaction of the acid and base from the releasing tablets. All samples show the desired blue color immediately after being prepared and prior to exposure of the indicator to high pressure to simulate HPP. However, all samples show the yellowish/green trigger color after three days of exposure but prior to exposure of the indicator to high pressure to simulate HPP.

Example 7

An acid releasing tablet is prepared by pressing 500 mg of solid organic acid (toluene sulfonic acid) in a 13 mm die (5.0 T/10 seconds).

A base releasing tablet is prepared by pressing 500 mg of solid base (sodium bicarbonate) in a 13 mm die (5.0 T/10 seconds).

A 10% Metacresol Purple (MCP) and Ethylene vinyl acetate (EVA) pH/carbon dioxide sensitive color changeable film is prepared as follows. 10 mL of a dye solution is prepared by adding water and Congo Red to achieve a dye concentration of 30 mg per mL of water. The dye solution is sonicated for at least 30 minutes to dissolve the dye. An ink is prepared by combining 7 ml of the dye solution, 20 g of 15% aqueous solution of PVA and an additional 3 ml of water. The ink solution is stirred. A film of the ink is cast on a PET plastic flexible sheet with k-bar no. 3 (ca. 23 microns wet thickness). The film is then allowed to dry. The film is a very deep blue color that changes to yellow in excess of carbon dioxide. This film is cut to circles 13 mm in diameter.

A non-porous washer or perforated disc made out of PVC is prepared. The PVC washers or perforated discs are 15 mm in diameter and vary in thickness from 0.25 to 2 mm. Some are mesh with 0.5 mm openings and others are washers with a single bore of 7.5 mm in diameter. Examples are shown at FIG. 12.

The four layers are assembled with the acid releasing tablet on the bottom, the washer/perforated disc on top of the acid releasing tablet, the base releasing tablet on top of the washer/perforated disc and the color changeable film on top of the base releasing layer.

The tablets, washer/perforated disc and color changeable films are vacuum sealed in a protectant made of aluminum oxide coated PET to form the pressure sensitive color changeable indicators.

The indicators are exposed to hydrostatic pressure of 300 MPa for 10 minutes to simulate HPP.

Figure 11:
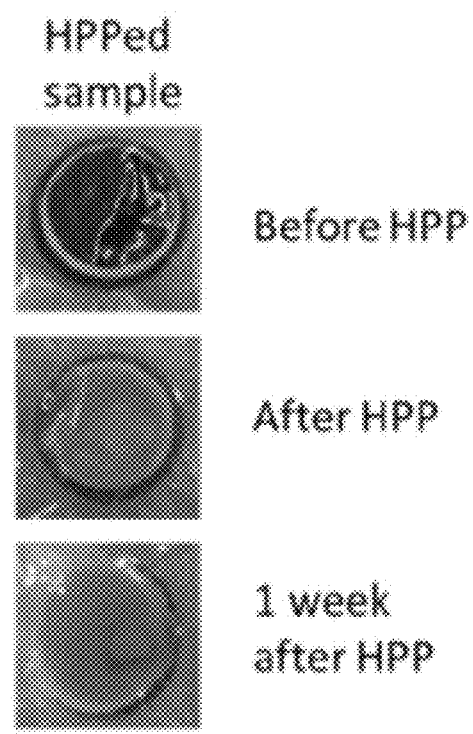

FIG. 11 shows the resulting color changeable indicators before exposure to high pressure to simulate HPP, after exposure to high pressure to simulate HPP and 1 week after exposure to high pressure to simulate HPP. The bluish color is the initial color of the MCP film prior to exposure of the film to higher carbon dioxide from reaction of the acid and base from the releasing tablets. The yellowish/green color is the triggered color of the MCP film after exposure of the film to carbon dioxide from the reaction of the acid and base from the releasing tablets. The samples (all washers/disc configurations at all thicknesses) show the desired blue color immediately after being prepared and prior to exposure of the indicator to high pressure to simulate HPP. The samples show the desired yellowish trigger color after exposure of the indicator to high pressure to simulate HPP. The samples maintain the yellowish color one week after exposure of the indicator to high pressure to simulate HPP.

While the application has been described with reference to certain embodiments, it will be understood by those skilled in the art that various changes may be made and equivalents may be substituted without departing from the scope of the application. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

The invention claimed is:

1. An indicator comprising:
a reagent releasing layer configured to release a reagent upon exposure to high pressure;
a transition layer disposed on said reagent releasing layer; and
a color changeable layer disposed on said transition layer;
wherein the transition layer is configured to allow permeation of the reagent to the color changeable layer upon exposure to high pressure and the color changeable layer is configured to change to a color upon exposure of the indicator to high pressure.

2. The indicator of claim 1 wherein the color changeable layer is configured to change color upon exposure of the indicator to high pressure pasteurization.

3. The indicator of claim 1 wherein the reagent releasing layer comprises an acid and water releasing tablet.

4. The indicator of claim 3 wherein the acid and water releasing tablet comprises an organic acid, hydrated particles, and polymer binder particles.

5. The indicator of claim 4 wherein the hydrated particles are hydrated to between 70% and 71% by weight.

6. The indicator of claim 2 wherein the transition layer is a permeable membrane.

7. The indicator of claim 6 wherein the permeable membrane has a pore size of up to about 0.2 microns.

8. The indicator of claim 6 wherein the permeable membrane has a pore size of up to about 0.03 microns.

9. The indicator layer of claim 1 wherein the reagent releasing layer comprises an acid releasing tablet.

10. The indicator of claim 9 wherein the transition layer is a permeable hydrated layer.

11. The indicator of claim 10 wherein the permeable hydrated layer is a silica doped hydrated layer.

12. The indicator of claim 11 wherein the silica doped hydrated layer comprises silica gel particles and binder particles.

13. The indicator of claim 12 wherein the silica gel particles are hydrated to between 70% and 71% by weight.

14. The indicator of claim 1 wherein the color changeable layer is a color changeable film.

15. The indicator of claim 14 wherein the color changeable film comprises a pH indicator.

16. The indicator of claim 14 wherein the high pressure is at least 450 MPa.

17. The indicator of claim 1 further comprising a protectant encompassing said reagent releasing layer, transition layer and color changeable layer.

18. The indicator of claim 17 further comprising an adhesive to apply the indicator to a substrate.

19. A packaging incorporating the indicator of claim 17.

20. The indicator of claim 1 wherein the color changeable layer is configured to change to a color after exposure to a predetermined amount of high pressure for a predetermined period of time.

21. The indicator of claim 20 wherein the color changeable layer is configured to change to a color after exposure to at least about 600 MPa for at least about 10 minutes.

22. A color changeable indicator comprising:
a first reagent releasing layer configured to release a reagent upon exposure to high pressure;
one or more additional reagent releasing layers;
a transition layer disposed between said first reagent releasing layer and said one or more additional reagent releasing layers, wherein the transition layer is configured to allow permeation of a reagent between said first reagent releasing layer and said one or more additional reagent releasing layers; and
a color changeable layer disposed on one of said one or more additional reagent releasing layers;
wherein the color changeable layer is configured to change to a color upon exposure of the indicator to high pressure.

23. The indicator of claim 22 wherein said first reagent releasing layer is an acid releasing tablet.

24. The indicator of claim 22 wherein said one or more of the additional reagent releasing layers comprises a sodium bicarbonate tablet.

25. The indicator of claim 22 wherein said color changeable layer comprises a pH indicator.

26. The indicator of claim 22 wherein the transition layer is comprised of non-permeable material in the form of a washer or a perforated disc.

27. The indicator of claim 22 further comprising a protectant encompassing said reagent releasing layers, transition layer and color changeable layer.

28. The indicator of claim 27 further comprising an adhesive to apply the substrate.

29. A packaging incorporating the indicator of claim 27.

* * * * *